United States Patent
Newman et al.

(10) Patent No.: US 8,851,078 B2
(45) Date of Patent: Oct. 7, 2014

(54) CHIN STRAP

(75) Inventors: Peter Lionel Harry Newman, Newtown (AU); Aaron Samuel Davidson, Mona Vale (AU); Justin John Formica, Voyager Point (AU); Anthony Paul Barbara, Smithfield (AU); Jose Ignacio Romagnoli, Redfern (AU); Dion Charles Chewe Martin, Concord (AU); Adam Barlow, Lilyfield (AU); Robert Henry Frater, Lindfield (AU)

(73) Assignee: ResMed Limited, Bella Vista (AU)

( * ) Notice: Subject to any disclaimer, the term of this patent is extended or adjusted under 35 U.S.C. 154(b) by 293 days.

(21) Appl. No.: 13/064,098

(22) Filed: Mar. 4, 2011

(65) Prior Publication Data

US 2011/0220113 A1 Sep. 15, 2011

Related U.S. Application Data

(60) Provisional application No. 61/282,602, filed on Mar. 5, 2010.

(51) Int. Cl.
*A61F 5/56* (2006.01)
*A61M 16/06* (2006.01)

(52) U.S. Cl.
CPC ....... *A61M 16/0683* (2013.01); *A61M 16/0694* (2013.01); *A61M 16/0633* (2013.01)
USPC ...................... 128/848; 128/207.11

(58) Field of Classification Search
USPC ............... 128/846, 848; 602/902; 482/10, 11; 606/204.35, 204.15
See application file for complete search history.

(56) References Cited

U.S. PATENT DOCUMENTS

| | | | | | |
|---|---|---|---|---|---|
| 649,896 | A | * | 5/1900 | Baughman | 128/848 |
| 1,339,865 | A | * | 5/1920 | Rothenberger | 128/848 |
| 1,471,839 | A | * | 10/1923 | Epling | 128/848 |
| 1,629,892 | A | * | 5/1927 | Storms | 128/848 |
| 1,990,411 | A | * | 2/1935 | Lowry | 128/848 |
| 3,572,329 | A | | 3/1971 | DeWoskin | |
| 4,703,879 | A | * | 11/1987 | Kastendieck et al. | 2/422 |
| 5,361,416 | A | | 11/1994 | Petrie et al. | |
| 5,687,743 | A | * | 11/1997 | Goodwin | 128/848 |
| 5,787,894 | A | * | 8/1998 | Holt | 128/848 |
| 5,893,365 | A | * | 4/1999 | Anderson | 128/848 |

(Continued)

FOREIGN PATENT DOCUMENTS

| | | |
|---|---|---|
| WO | WO 2007/147088 | 12/2007 |
| WO | WO 2009/052560 | 4/2009 |
| WO | WO 2010/139014 | 12/2010 |

OTHER PUBLICATIONS

Fitzpatrick et al., "Effect of nasal or oral breathing route on upper airway resistance during sleep," Eur Respir J 2003: 22:, pp. 827-832.

(Continued)

*Primary Examiner* — Patricia Bianco
*Assistant Examiner* — Raymond E Harris
(74) *Attorney, Agent, or Firm* — Nixon and Vanderhye P.C.

(57) ABSTRACT

A chin strap includes a chin cup, side straps, and rear straps. The chin strap is used to urge the patient's jaw upwards and substantially close the patient's mouth while pressurized breathable gas is delivered to the patient's nose by the mask system.

38 Claims, 21 Drawing Sheets

(56) References Cited

U.S. PATENT DOCUMENTS

| | | | |
|---|---|---|---|
| 6,016,807 A * | 1/2000 | Lodge | 128/848 |
| 6,119,694 A | 9/2000 | Correa et al. | |
| 6,277,053 B1 * | 8/2001 | Desembrana | 482/11 |
| 6,279,577 B1 * | 8/2001 | Savaiano | 128/848 |
| 6,860,268 B2 | 3/2005 | Bohn et al. | |
| 6,926,004 B2 | 8/2005 | Schumacher | |
| 7,000,611 B2 | 2/2006 | Klemperer | |
| 7,000,615 B2 | 2/2006 | Taylor-Kennedy | |
| 7,225,811 B2 * | 6/2007 | Ruiz et al. | 128/207.11 |
| 7,331,349 B2 * | 2/2008 | Brady et al. | 128/848 |
| 2004/0226566 A1 * | 11/2004 | Gunaratnam et al. | 128/207.18 |
| 2005/0277821 A1 | 12/2005 | Payne, Jr. | |
| 2007/0181135 A1 * | 8/2007 | Baker | 128/848 |

OTHER PUBLICATIONS

Vorona et al., "Treatment of Severe Obstructive Sleep Apnea Syndrome with a Chinstrap," JCSM Journal of Clinical Sleep Medicine, vol. 3, No. 7 (2007), pp. 729-730.

Madronio et al., "Older individuals have increased oro-nasal breathing during sleep," Eur Respir J 2004: 24: pp. 71-77.

http://www.amazon.com/s/ref=nb_sb_ss_c_1_10?url=search-alias%3Dhpc&field-keywords=chinstraps&sprefix=chinstraps; 11 pages, including: "Respironics Premium Chinstrap;" "SP Medical Adjustable CPAP Chin Strap;" "Respironics Premium Chin Strap;" "AG Industries Deluxe CPAP Chinstrap III Around Ear (Black);" "Puresom Ruby Adjustable CPAP Chin Strap;" "AZIZA CPAP Chinstrap—Stays in place during sleep;" "CPAP Chin Strap—100% Cotton—Adjustable—SM;" "Avalon Aire Ruby Chin Strap—Medium;" "SP Medical Puritan Bennett Style CPAP Chin Strap;" "Topaz Style Chin Strap—Adjustable;" "Respironics Style Premium Chin Strap;".

"Regular chinstrap 1/pk;" "CPAP Universal Chinstrap, Ea;" "Super Deluxe Chin Strap—Large;" "Ruby Adjustable Chin Strap, Fits 3 Sizes Small Thru Large;" "PB Style Neoprene CPAP Chin Strap;" "Puresom Ruby Adjustable Extra Large CPAP Chin Strap;" "C Pap Chin Strap;" "Topaz Adjustable Chin Strap-XL;" "SP Medical Royal Crown Adjustable CPAP Chin Strap;" "CPAP Chin Strap—100% Cotton—Adjustable—L-XL;" "Chin Strap, Extra Large—Respironics Style;" "Respironics Premium-Style Chin Strap—1 each;" "Resmed Style Blue Chin Strap;" "Super Deluxe Chin Strap;" "Topaz Adjustable Chin Strap;" "Deluxe Chin Strap;" "Ruby Chin Strap Adjustable XL;" "Ruby Chin Strap Made with Breath-o-prene, Large, 1 each;" "Chin Strap—Tiara PureSom Ruby Topaz Adjustable, 1/ea;" "Deluxe Chin Strap—1 each (Size = Large);" and "Premier Style Chin Strap, 1/Ea.", acquired at least by May 25, 2011, USPTO to assume before Applicant's filing date*.

* cited by examiner

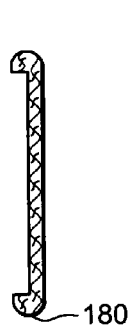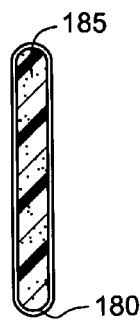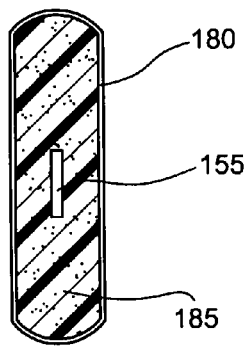
FIG. 11A  FIG. 11B  FIG. 11C
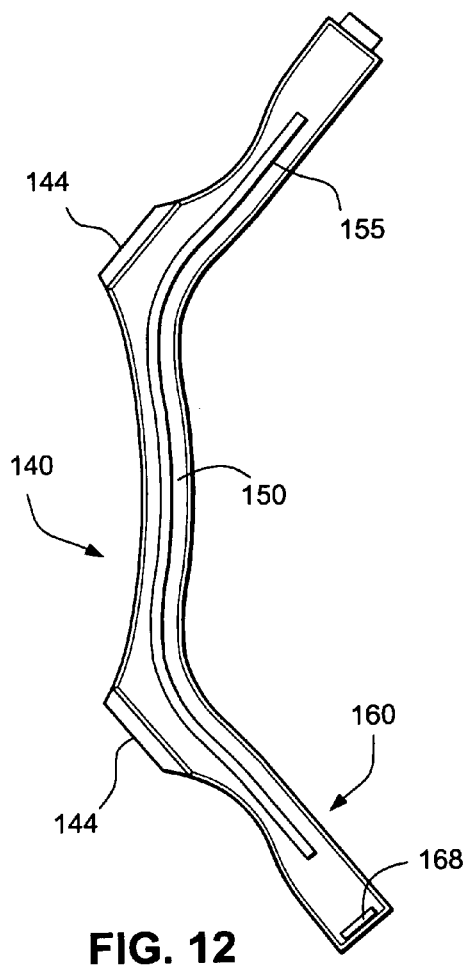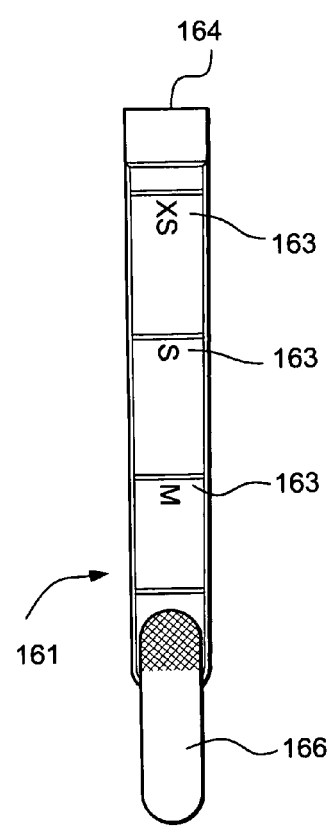
FIG. 12  FIG. 13

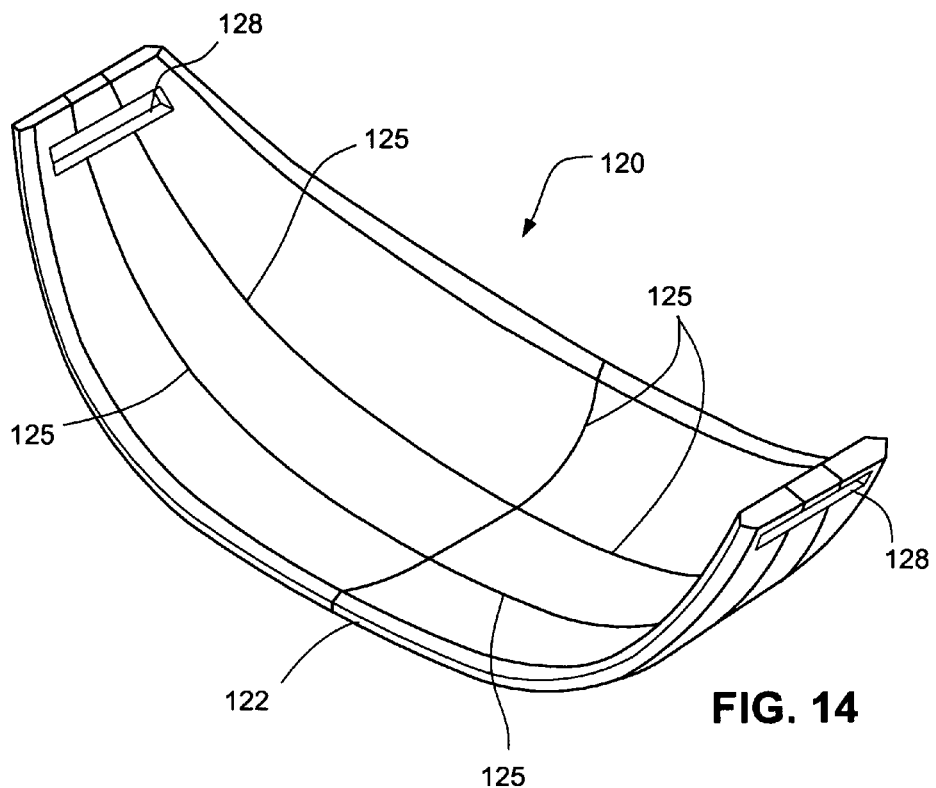
FIG. 14
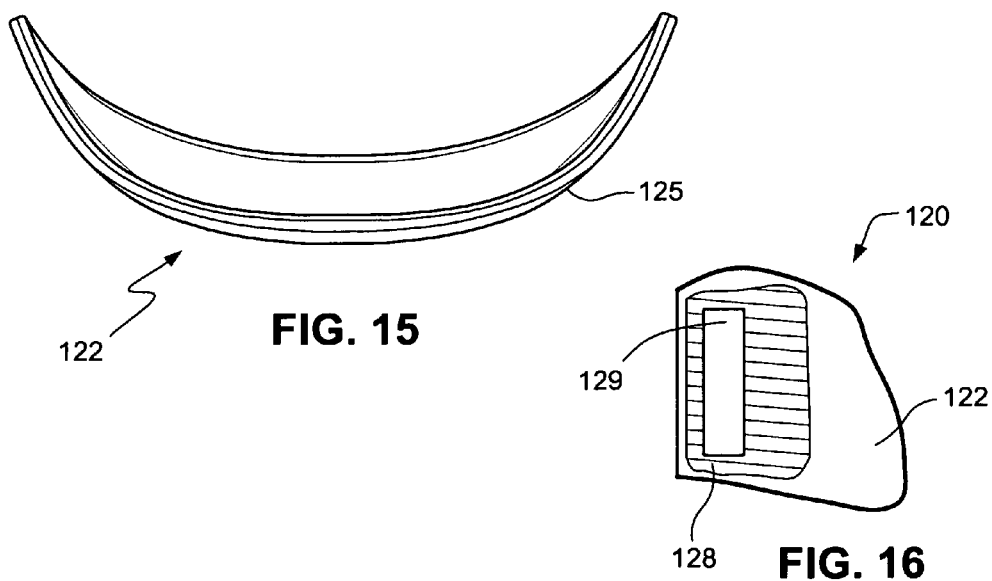
FIG. 15
FIG. 16

CHIN STRAP

CROSS-REFERENCE TO APPLICATION

This application claims the benefit of U.S. Provisional Application No. 61/282,602, filed Mar. 5, 2010, which is incorporated herein by reference in its entirety.

FIELD OF TECHNOLOGY

The present technology relates to a chin strap and a method of manufacturing the chin strap for use in assisting the patient to maintain a closed mouth. The chin strap may be used with a mask, the mask being used for treatment, e.g., of Sleep Disordered Breathing (SDB) with Continuous Positive Airway Pressure (CPAP) or Non-Invasive Positive Pressure Ventilation (NIPPV).

BACKGROUND OF TECHNOLOGY

Chin straps can be optionally used by a patient when wearing a mask for treatment of SDB such as OSA. When wearing a mask that delivers treatment to the patient through their nose, some patients have a tendency to open their mouth or drop their jaw such that treatment can be ineffective. Therefore, for patients who have a tendency to open their mouth it can be desirable to assist them in keep their mouth closed during treatment to ensure treatment is effective.

FIGS. 1 and 2 show prior art chin strap arrangements. Typical chin straps 1 include at least a chin cup 20, side straps 40 and/or rear strap 60.

Chin cup 20 may engage with the patient's chin or jaw region and transfer the forces from the chin strap 1 to the patient. Side straps 40 may extend from the chin cup, along the side of the patient's cheek bones and over the top of the patient's head. Rear strap 60 may engage a posterior or rear region of the patient's head.

FIG. 1 shows a prior art chin strap arrangement 1. This arrangement may be unstable as it has only one pair of side straps 40 that may easily become dislodged or displaced during the patient's sleep. In addition, this arrangement provides a force on the patient's chin in the vertical and horizontal direction since the side straps 40 are angled from the vertical direction. This means that there is a force that may push the patients jaw towards their neck region, causing additional force on the patient's neck. This may be uncomfortable as well as exacerbating the collapse of their airways. Furthermore, the chin cup 20 of the prior art chin strap arrangement 1 is not contoured to the shape of the patient's chin so may be uncomfortable.

FIG. 2 shows another prior art chin strap arrangement 1. This arrangement has wide straps and thus covers a large portion of the patient's face when in use. This may be uncomfortable and obtrusive. Furthermore, extended use of a chin strap can lead to warming or a temperature increase of the patient's skin proximal to the straps. The thickness of the straps may mean that more heat is retained and hence the patient may feel discomfort due to the increased warmth.

A chin strap that is effective in maintaining the mouth in a closed position, is comfortable to wear with a mask, and is inexpensive is needed in the art.

SUMMARY OF TECHNOLOGY

A first aspect of the present technology is to provide a chin strap, e.g., for use as a stand-alone device or with a mask, that assists in maintaining a patient's mouth in a substantially closed position.

Another aspect of the present technology is to provide a chin strap that is comfortable for a patient to wear.

Another aspect of the present technology is to provide a chin strap that is able to be manufactured inexpensively.

Another aspect of the present technology is to provide a chin strap that is stable when in use.

Another aspect of the present technology is to provide a chin strap that provides a generally vertically upwards force on chin to assist in maintaining the patient's mouth substantially closed.

Another aspect of the present technology is to provide a chin strap that provides minimal force in the generally horizontal plane to prevent additional weight being imposed on the collapsible region of the patient's airways.

Another aspect of the present technology is to provide inextensible portions of the chin strap to stabilize and position the chin strap on the patient's head.

Another aspect of the present technology is to provide adjustment on the chin strap to advantageously fit a wide variety of patients.

Another aspect of the present technology is to provide adjustment to the straps along the patient's cheek bone in a generally upwards direction to advantageously provide easy adjustment of the strap length and hence force provided to the patient's chin.

Another aspect of the present technology is to provide a conformable chin cup to comfortably engage the chin of a patient.

Another aspect of the present technology is a chin strap with strap connections formed with the chin cup.

Another aspect of the present technology relates to a chin strap including a chin cup, a side strap, and a rear strap, wherein the chin cup is preformed to a shape that closely matches a patient's chin shape and has an integrally attached connector for receiving a side strap.

Another aspect of the present technology relates to a chin strap including a chin cup, side straps provided to respective sides of the chin cup, a rear strap, and a strap connecting member to interconnect the side straps and the rear strap. The strap connecting portion includes a portion adapted to extend over the top of the patient's head, first connectors for attaching respective side straps, and second connectors for attaching the rear strap.

Another aspect of the present technology relates to a chin strap arrangement including a side strap portion adapted to extend along the side of the patient's head and forward of the patient's ear and including a cantilever arm adapted to extend along the patient's cheek, and a chin strap portion provided to the cantilever arm and adapted to extend under the patient's chin.

Another aspect of the present technology relates to a mask arrangement including a chin strap arrangement and a mask system structured to deliver pressurized breathable gas to a patient's airways. The chin strap arrangement includes a chin engaging portion and headgear to support the chin engaging portion in position on the patient's head in use. The chin engaging portion is preformed to a shape that closely matches a patient's chin shape. The mask system includes a sealing interface adapted to form a seal with the patient's nose and/or mouth and mask headgear straps provided to the sealing interface. The mask headgear straps are structured to releasably engage side straps of the headgear to support the mask system in position on the patient's face in use.

Another aspect of the present technology relates to a chin strap arrangement that provides a substantially vertically upwards vector or force component to the patient's chin or jaw, and minimizes an anterior-posterior force component so as to minimize anterior-posterior displacement of the jaw.

Other aspects, features, and advantages of this technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various examples of this technology. In such drawings:

FIG. 11A is cross-section through line 11A-11A shown in FIG. 10;

FIG. 11B is cross-section through line 11B-11B shown in FIG. 10;

FIG. 11C is cross-section through line 11C-11C shown in FIG. 10;

FIG. 12 shows straps of a chin strap arrangement according to an example of the present technology;

FIG. 13 shows indicators for straps of a chin strap arrangement according to an example of the present technology;

FIG. 14 is a perspective view of a chin cup for a chin strap arrangement according to an example of the present technology;

FIG. 15 is a front view of the chin cup of FIG. 14;

FIG. 16 is a side view of the chin cup of FIG. 14;

DETAILED DESCRIPTION OF ILLUSTRATED EXAMPLES

Figure 1:
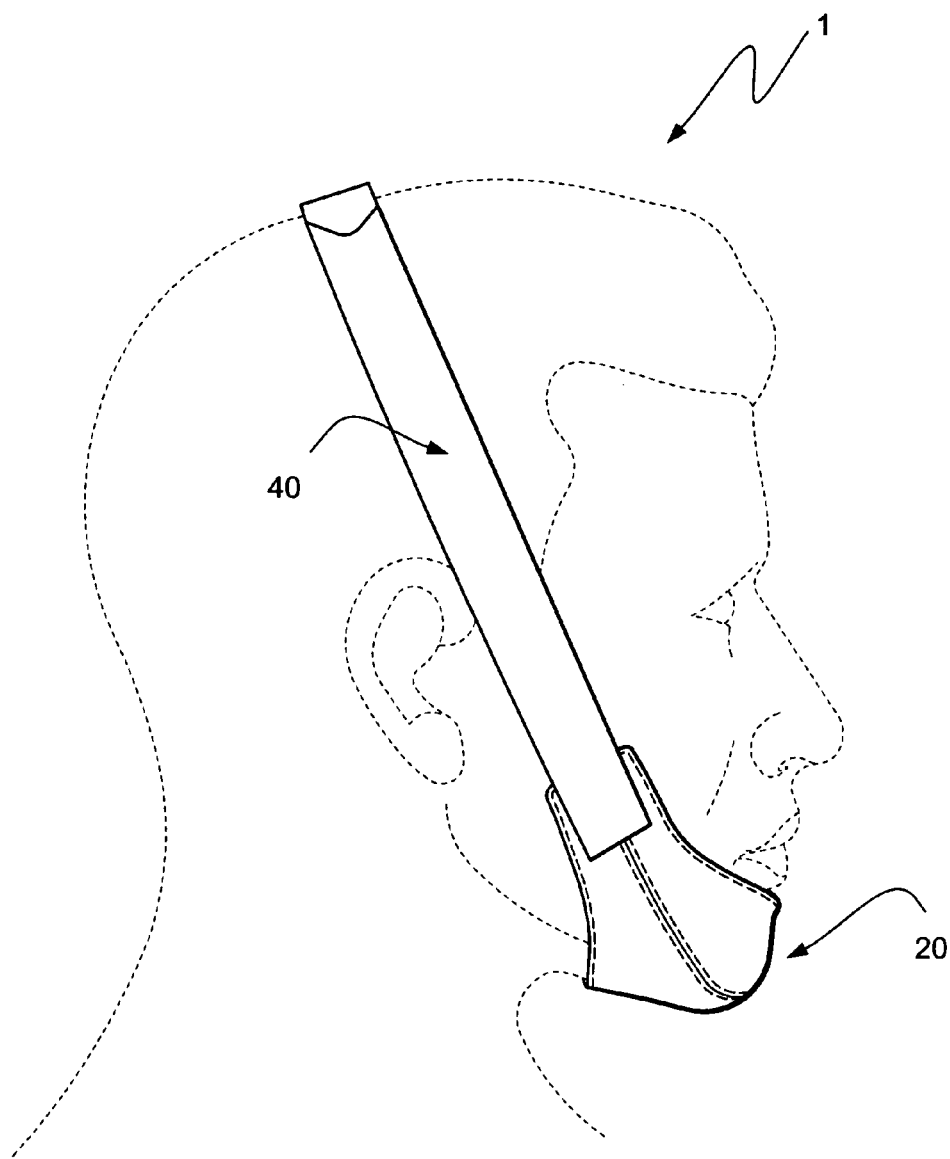
FIG. 1 shows a prior art chin strap arrangement.
Figure 2:
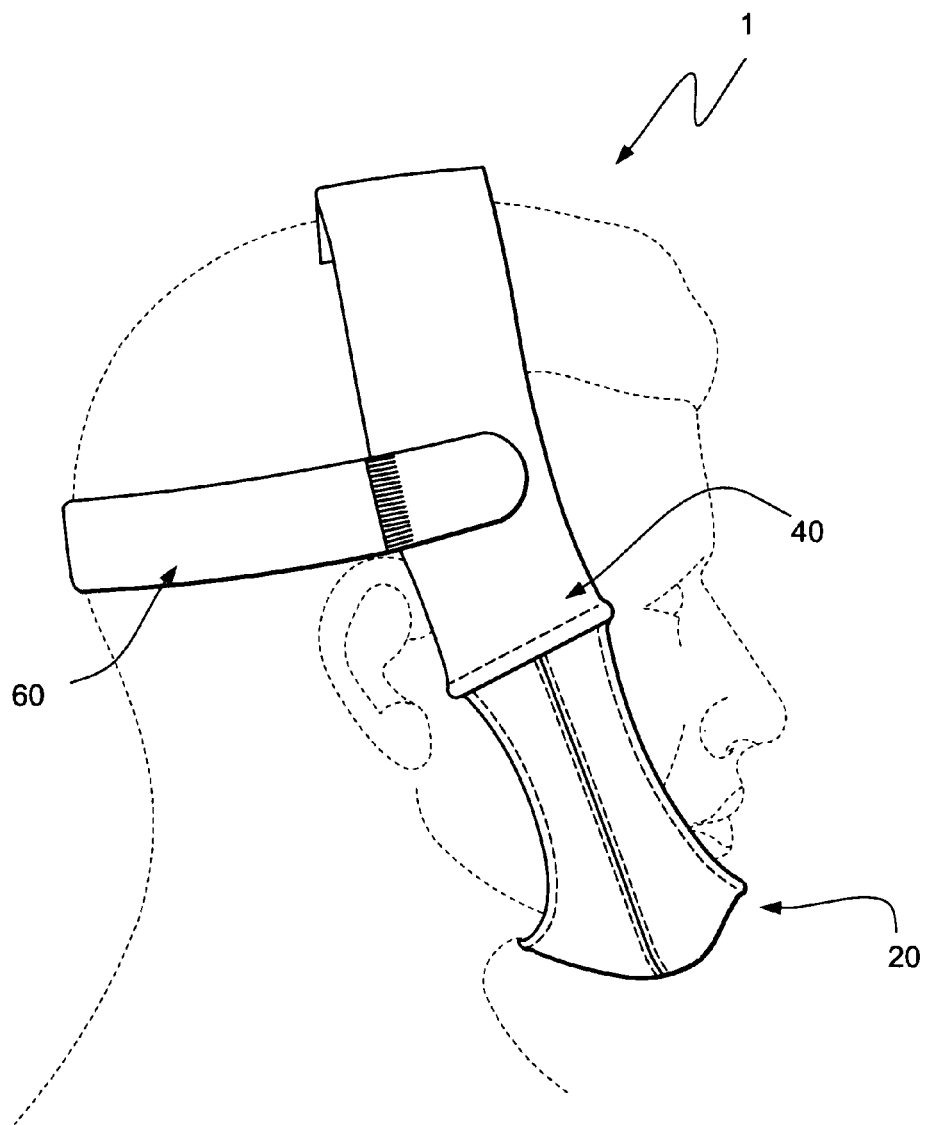
FIG. 2 shows another prior art chin strap arrangement.

The following description is provided in relation to several examples (most of which are illustrated, some of which may not) which may share common characteristics and features. It is to be understood that one or more features of any one example may be combinable with one or more features of the other examples. In addition, any single feature or combination of features in any example or examples may constitute patentable subject matter.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

"Rigidizer" means and includes any reinforcing element that increases the rigidity of another item and may include an object that improves rigidity in one or more axes. "Rigidizer" may further include any element that increases the stiffness or reduces the extensibility of another item.

1. Chin Strap

A chin strap according to an example of the present technology is structured to discourage jaw opening during sleep, with or without concurrent CPAP therapy. For example, the chin strap may be provided as a mouth closure device structured and arranged to provide stand-alone therapeutic benefits, e.g., SDB therapy, snoring therapy (e.g., chin strap is an SDB device by itself, which can treat some forms of obstructions without supplying CPAP at all). In another example, the chin strap may be provided to a mask system to enhance treatment of SDB. In such example, a chin strap may be provided for use along with an existing mask harness or headgear of the mask system (e.g., chin strap attaches to mask headgear to support upward force for jaw closure). Alternatively, the chin strap may be integral with a mask harness or headgear of the mask system, e.g., mask headgear includes chin strap.

In an example, the chin strap may include one or more of the following aspects: comfortable mouth closure without rearward displacement (e.g., for minimizing upper airway restriction (UAR)); permit forceful mouth opening, (e.g., for risk mitigation of nasal obstruction and for speech); stabilize the jaw in place; light and/or minimal encumbrance; cool and comfortable; aesthetically appealing; and/or re-usable and washable (e.g., minimum three-month endurance).

In an example, the chin strap may include a form of cap/frame and a semi-rigid flat-profile shape which the support (e.g., elastic support) is attached to. Sufficient rigidity is provided in the direction of support to the jaw, but lateral deformation is provided to fit to the face and to deform with the face when the patient is lying down, e.g., on a pillow.

In an example, the chin strap may be integrated with mask headgear for a mask system, i.e., combined headgear and chin strap arrangement, e.g., for when a chin strap is desired with nasal CPAP. This arrangement allows a combined device rather than having to wear both a headgear arrangement and a chin strap arrangement.

In an example, a chin strap is structured and arranged to provide a force on the patient's jaw to substantially close their mouth while receiving a supply of pressurized breathable gas through their nares.

Figure 3:
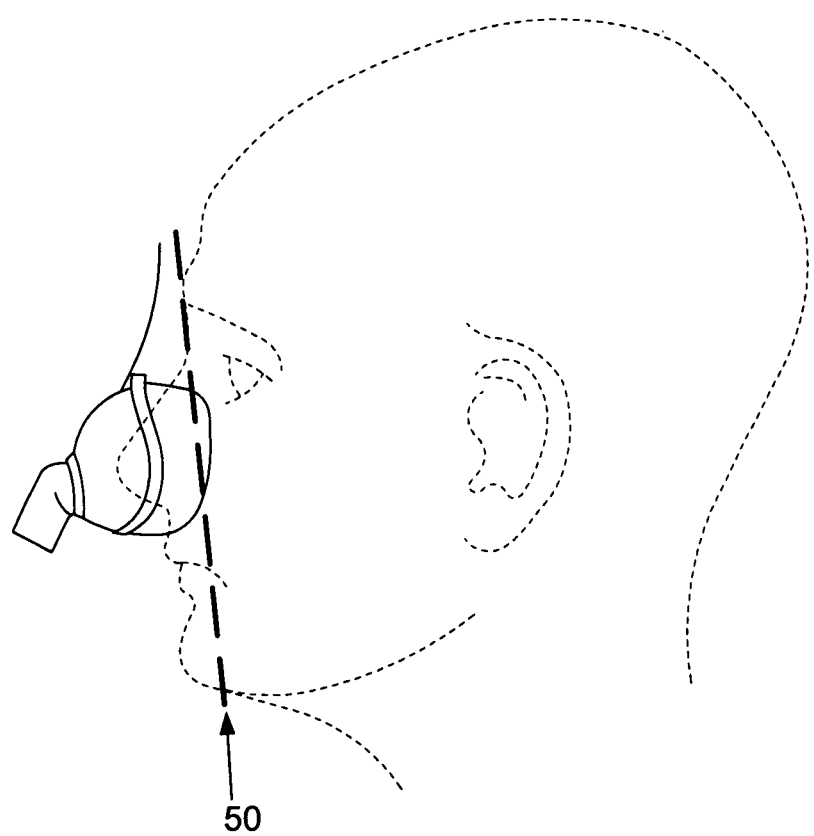
FIG. 3 demonstrates a preferred vector or force to be applied to the patient's jaw or chin by a chin strap.

Preferably, the chin strap will provide at least a substantially vertically upwards vector to the patient's chin or jaw to maintain the mouth in a closed position. FIG. 3 demonstrates the preferred vector or force 50 to be applied to the patient's jaw or chin.

In an example, the chin strap provides a substantially vertically upwards vector or force component to the patient's chin or jaw, and minimizes an anterior-posterior force component so as to minimize anterior-posterior displacement of the jaw. The chin strap is structured to mimic the direction of the forces that close the jaw, such as masseter muscle. That is, the chin strap is structured to close the patient's mouth or jaw, not retract the jaw which may make obstructions more likely.

In an example, the chin strap may be structured to provide an outward force vector to force the jaw forward.

In an example, the chin strap may be at least partially supported by the frame of the mask system.

Preferably, the chin strap may be comfortable so that the patient can wear the chin strap, e.g., with a mask system, for the duration of the patient's sleep.

Preferably, the chin strap may be stable on the patient's head to ensure that the substantially vertical vector is provided to the jaw or chin for a substantial portion of the patient's sleep.

Preferably, the chin strap may have an unobtrusive appearance so that patients will wear the chin strap.

2. Chin Strap Example With Nasal Mask

Figure 4:
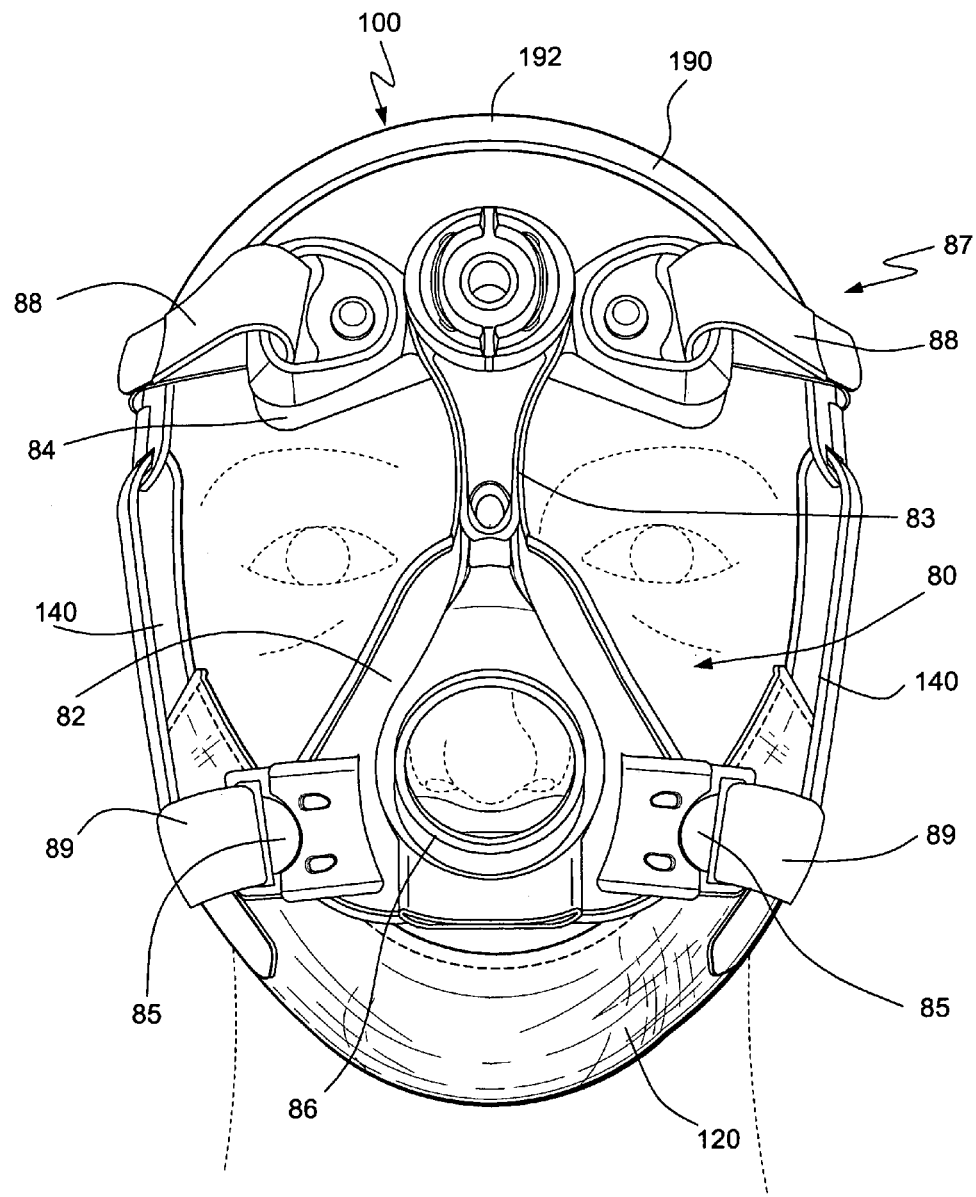
FIG. 4 is a front view of a mask system in use with a chin strap arrangement according to an example of the present technology.
Figure 5:
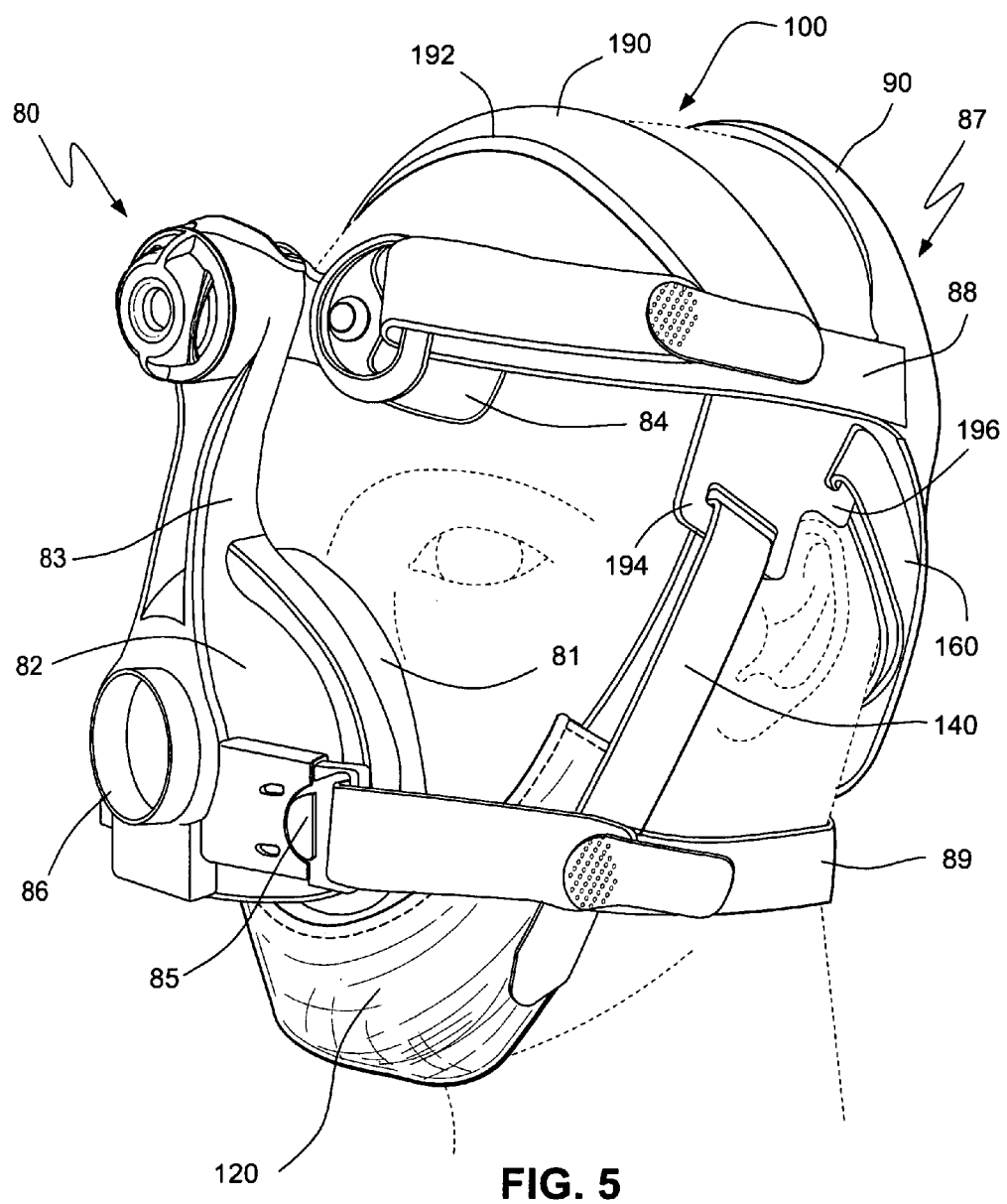
FIG. 5 is a perspective view of the mask system and chin strap arrangement of FIG. 4.
Figure 6:
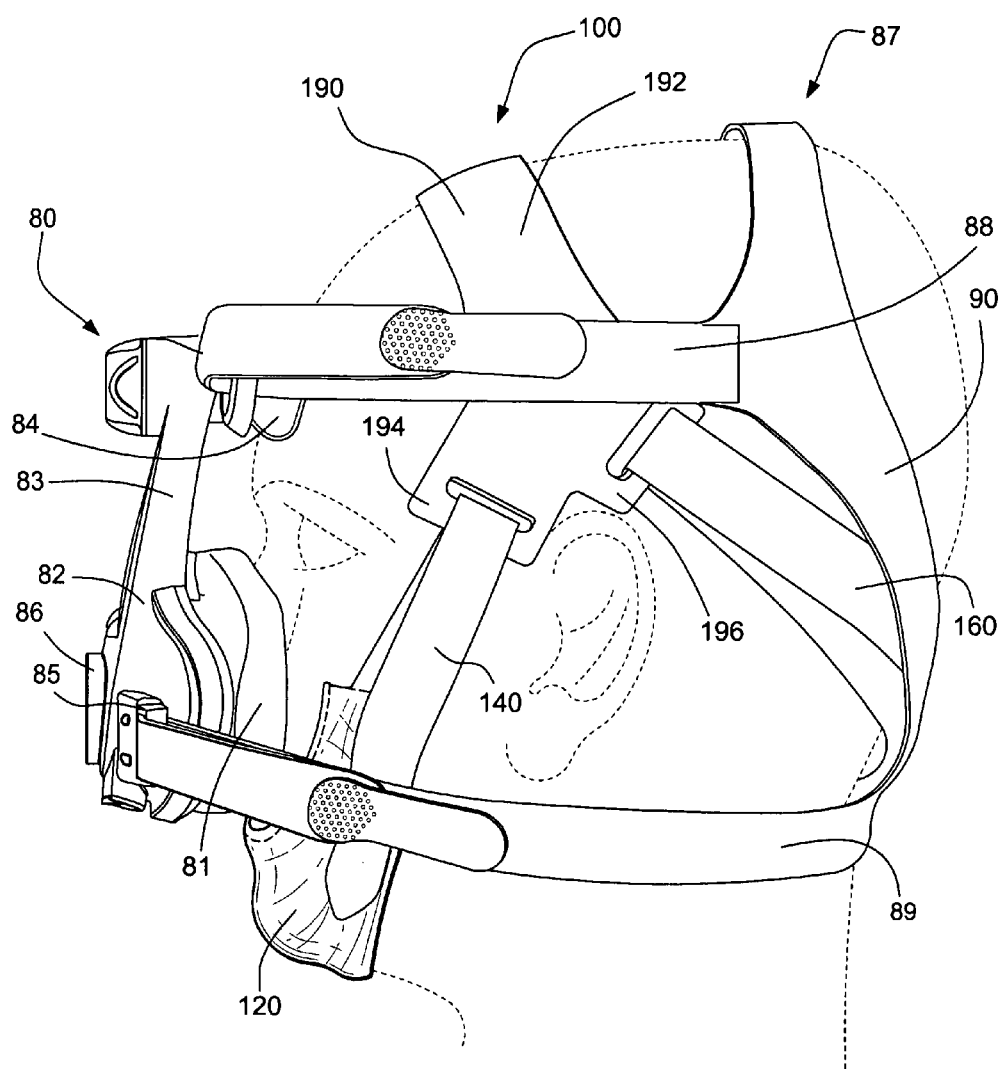
FIG. 6 is a side view of the mask system and chin strap arrangement of FIG. 4.

FIGS. 4 to 6 show a chin strap arrangement 100 in use with a mask system 80 (e.g., nasal mask) according to an example of the present technology. The mask system 80 may be used to deliver pressurized breathable gas to a patient's airways. The mask system 80 according to an example of the present technology may preferably deliver the pressurized breathable gas to the nose of the patient. This may include nasal masks, pillows masks, prongs, cradles or any other mask that delivers pressure to the nasal passages. However, as described above, it should be appreciated that the chin strap arrangement may be used as a stand-alone device, e.g., without a mask, to provide therapeutic benefits, e.g., SDB therapy, snoring therapy, etc.

The mask system 80 may include some or all of cushion 81, frame 82, forehead support 83, forehead pad 84, headgear connectors 85, air inlet 86 and headgear 87. Cushion 81 may contact and seal with the patient's face. The cushion may be made from a flexible material such as silicone, gel, foam or any other reasonable material. Cushion 81 may be a flap type seal, a compression seal, or any other sealing mechanism known in the art. Frame 82 is structured to engage with and position cushion 81 in the desired location on the patient's face and connects headgear 87 to stabilize cushion 81. Frame 82 may be generally inextensible or substantially rigid or semi-rigid and made from materials such polycarbonate, polypropylene, silicone or any other reasonable material. Forehead support 83 may be connected to frame 82 and may assist in stabilizing the cushion and allowing adjustment of the cushion position. Forehead support pad 84 may connect to forehead support 83 and contact the patient's forehead in use to increase the comfort of using a forehead support. Headgear 87 may include a plurality of straps. In the example shown, the headgear may include a pair of upper straps 88 and a pair of lower straps 89. Other arrangements are also possible (e.g., a single pair of straps, three straps, etc.). Upper headgear straps 88 may connect to forehead support 83 and lower headgear straps 89 may connect to frame 82 using headgear connectors or clips 85. Headgear may also include a rear strap 90 to engage the rear of the patient's head in use.

Preferably, the chin strap arrangement 100 may be positioned underneath mask system 80. Alternatively, mask system 80 may first be positioned on the patient's head and the chin strap arrangement 100 may be positioned over the mask system 80.

The chin strap arrangement 100 according to an example of the present technology includes a chin cup or chin engaging portion 120, a pair of side straps 140 and a rear strap 160.

2.1 Chin Cup

Figure 8:
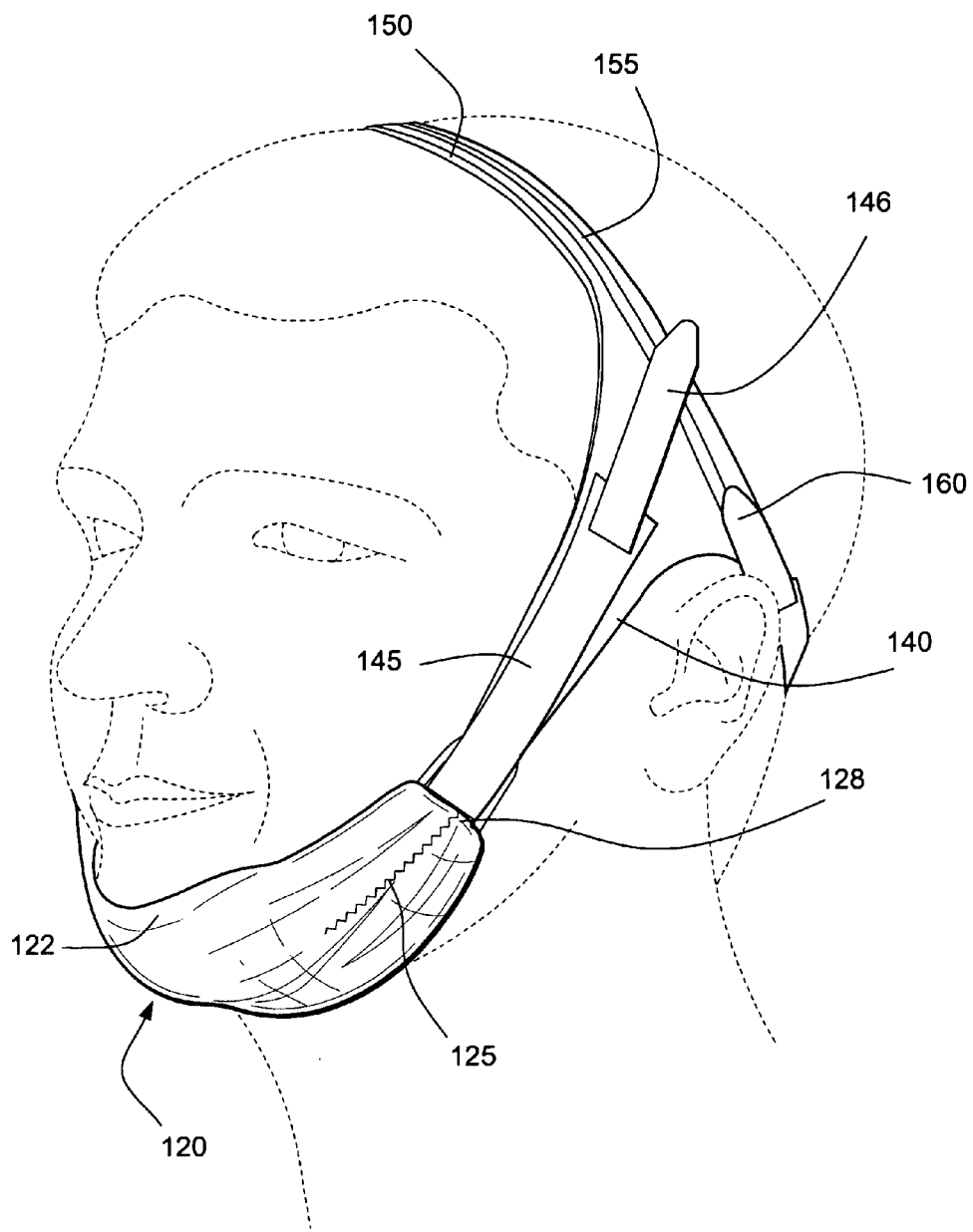
FIG. 8 shows a chin strap arrangement in use according to an example of the present technology.
Figure 9:
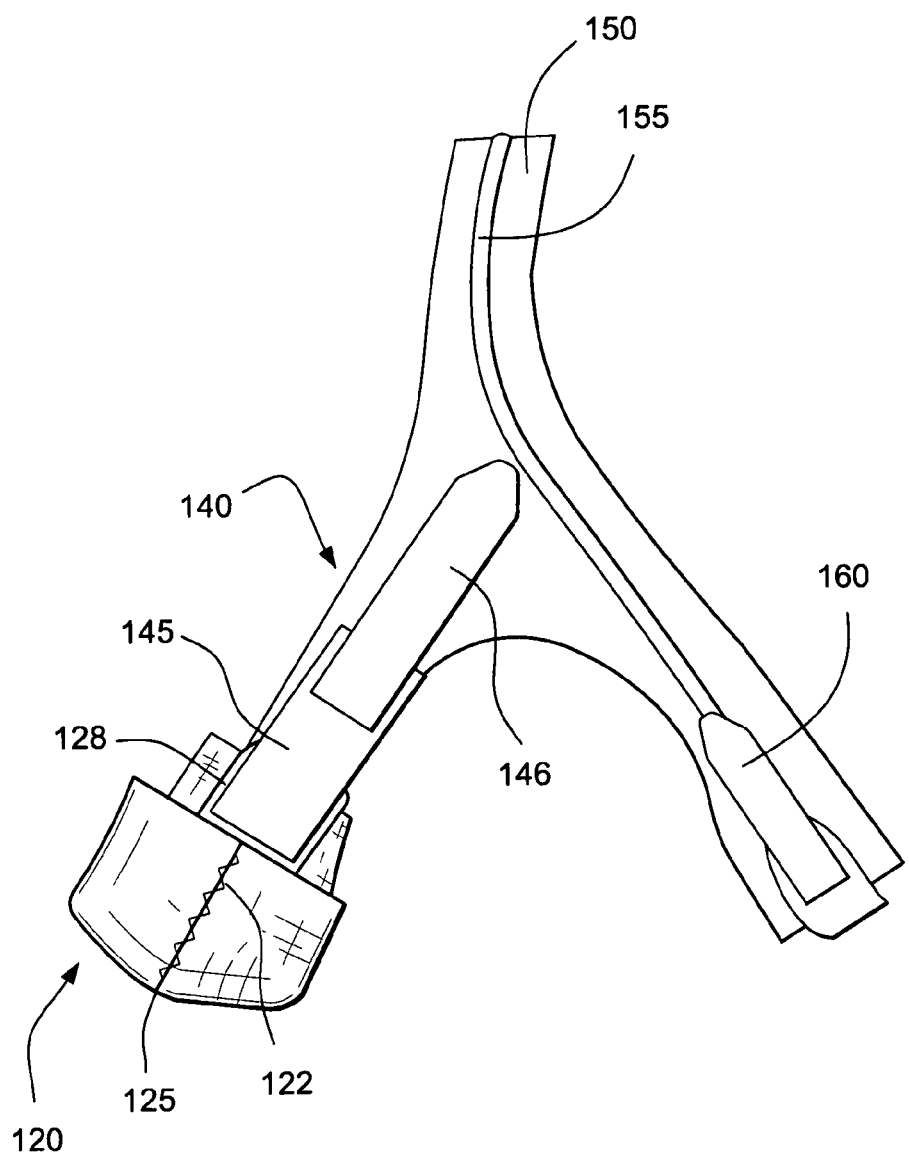
FIG. 9 shows a chin strap arrangement according to an example of the present technology.
Figure 10:
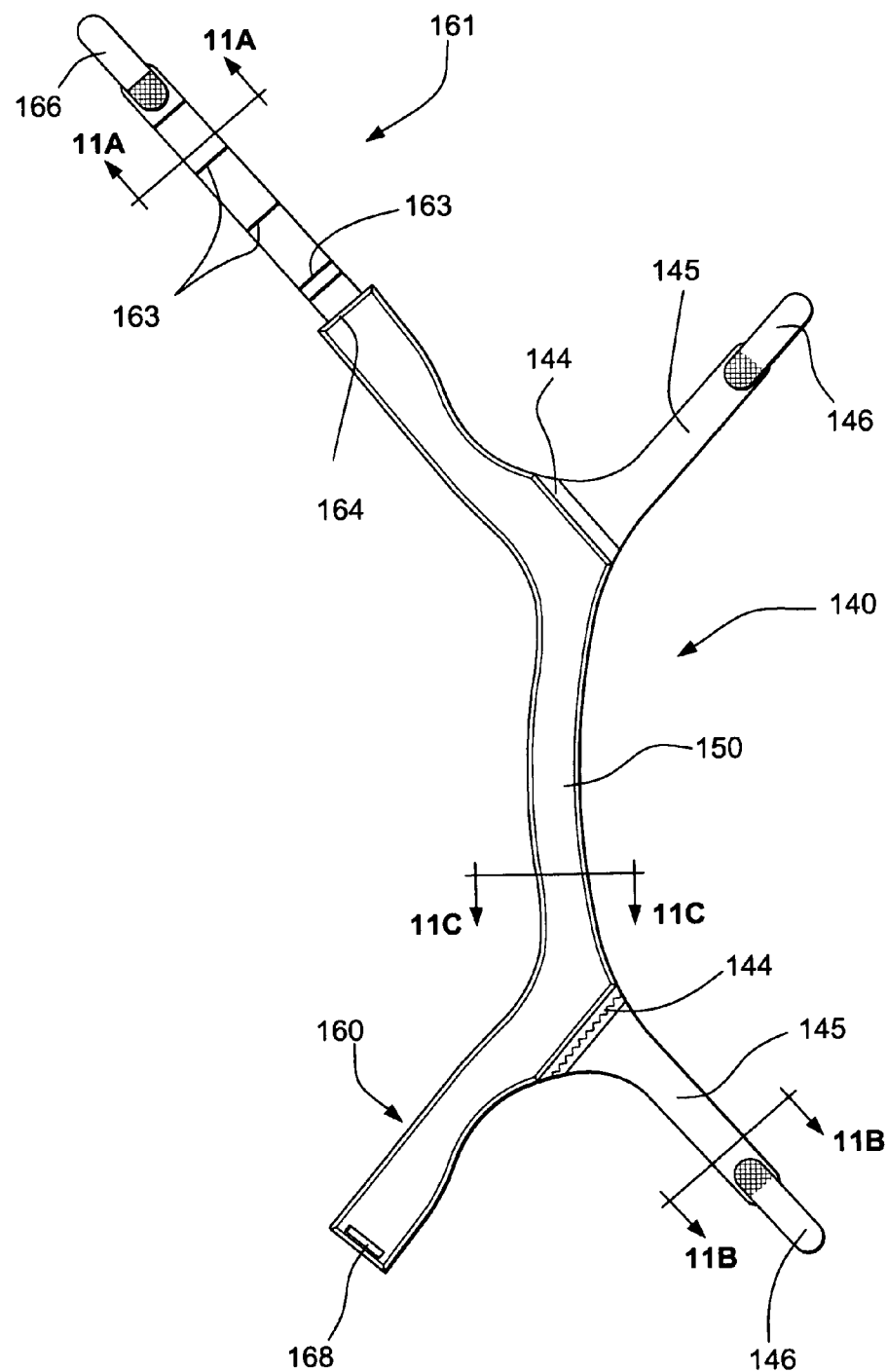
FIG. 10 shows a plan view of a chin strap arrangement according to an example of the present technology.

Chin cup 120 may include a formed region 122 and at least one attachment portion 128. Formed region 122 may cup or engage with the patient's chin. Formed region 122 may include at least one arc portion 125 that may shape the formed region into a generally curved shape that may mirror or closely relate to the shape of a patient's chin. Arc portion 125 may further enable chin cup 120 to flex or hinge about the arc portion to better conform chin cup 120 to the patient's chin geometry. Arc portion 125 may be ridges or planes formed into the cup (see FIG. 14 for example) or may be applied to a flat chin cup for example by stitching as shown in FIGS. 8 and 9. FIG. 15 shows a section through chin cup 120 demonstrating the shape of arc portion 125.

In an example, the chin cup is preformed to a shape that closely matches a patient's chin shape. That is, the chin cup includes its curved, preformed shape before being engaged with the patient's chin.

Figure 7:
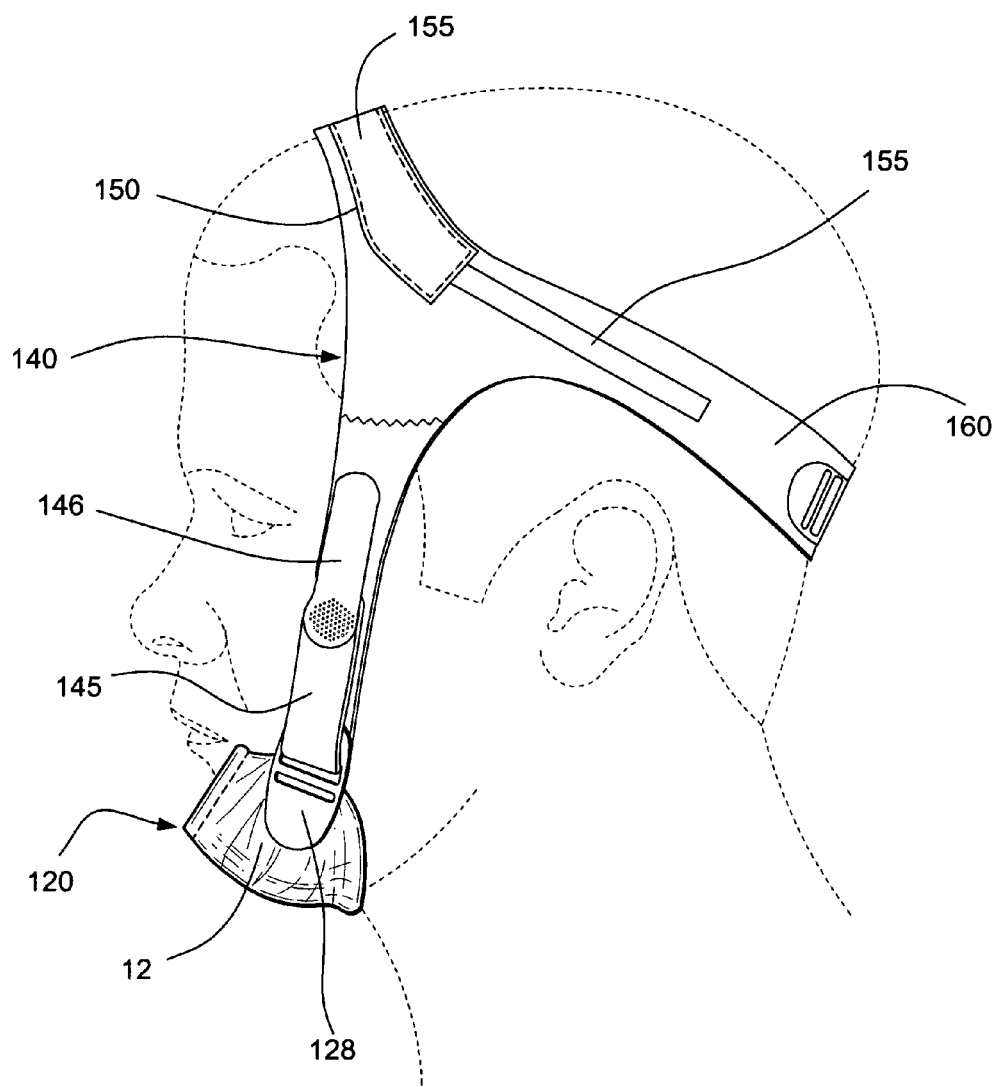
FIG. 7 shows a chin strap arrangement in use according to an example of the present technology.

FIGS. 14 to 16 show the chin cup. FIGS. 7 and 8 show the chin strap 100 in use, further showing the chin cup 120 in position.

Chin cup 120 may be constructed of a fabric. Preferably, chin cup 120 may be constructed of a formed fabric such as a thermoformed fabric, a stitched fabric, 3D woven fabric or combination thereof. Additionally, the fabric may be a lamination of, including but not limited to, two outer layers of fabric and an inner layer of foam.

Chin cup 120 may be die cut, ultrasonically die cut, molded or any other possible forming process.

Chin cup 120 may also be made from a skinned or unskinned foam.

Chin cup 120 may also be made from a gel. The gel may be encapsulated by a bladder.

Attachment portion 128 may optionally be molded with or formed into chin cup 120. FIG. 16 shows an attachment portion 128 within formed portion 122. Attachment portion 128 includes apertures 129 for receiving a strap.

2.2 Side Straps

Side straps 140 connect to chin cup 120 and direct a force upwards, substantially vertically upwards as shown in FIG. 3.

Side straps 140 include cheek portions 145 and top portion 150.

Cheek portions 145 are positioned in use along the patient's cheek bone or side of face. Cheek portion 145 may loop through aperture 129 in attachment portion 128 on chin cup 120. Cheek portion 145 may include a connector 146 to attach the loose end of the strap. This may be a hook and loop attachment, clip attachment, etc. Preferably, cheek portions 145 may be pulled upwards or towards the patient's ears or eyes to shorten the length and hence tighten the side straps 140. This may be easier for the patient to adjust than reverse arrangement.

Cheek portion 145 may be constructed of a fabric. Cheek portion 145 may preferably be constructed of a fabric and foam lamination. FIG. 11B shows a fabric outer layer 180 and a foam inner layer 185. Cheek portions 145 may be cut using die cutting, ultrasonic die cutting, or any other means.

Cheek portions 145 and top portion 150 may connected at junction 144. Junction 144 may be an ultrasonic weld, stitch, glue or other joining operation.

Top portion 150 is positioned in use over the top of the patients head, approximately in the region of the coronal suture.

At least a portion of top portion 150 may include a rigidiser or inextensible element to reduce the stretch of this portion of the side straps 140. Top portion 150 is preferably less extensible than cheek portions 145 so as to stabilize and position the chin strap 100.

Top portion 150 may be constructed of a fabric. Top portion 150 may preferably be constructed of a fabric and foam lamination. Top portion 150 may be cut using die cutting, ultrasonic die cutting, or any other means.

Top portion 150 may have a rigid element 155 attached or otherwise formed with the material of top portion 150. Preferably, rigid element 155 may be stitched, glued or otherwise attached to top portion 150. Most preferably, rigid element 155 may be formed or encapsulated in top portion 150. FIG. 11C shows a fabric outer layer 180, a foam inner layer 185 and a rigid element 155 extending there between or within the fabric layer.

As shown in FIGS. 4-6, a strap connecting member 190 may interconnect the side straps 140 and the rear strap 160. As illustrated, the strap connecting portion 190 includes a portion 192 adapted to extend over the top of the patient's head, first connectors 194 including slots for attaching respective side straps 140, and second connectors 196 including slots for attaching the rear strap 160.

2.3 Rear Strap

Rear strap 160 may be positioned at the rear of the patient's head, preferably capturing the occipital region of the patient's head. By engaging the occupant as shown in FIG. 7, rear strap 160 may be secured in position thereby stabilizing chin strap 100.

At least a portion of rear strap 160 may include a rigidiser or inextensible element to reduce its stretch or extensibility. The rigidiser in this region may stabilize and position rear strap 160 so that side straps 140 avoid contacting the patient's ears.

Rear strap 160 may be constructed of a fabric, elastic, plastic, foam, or any combination of these materials. Rear strap 160 may preferably be constructed of a fabric and foam lamination. Rear strap 160 may be cut using die cutting, ultrasonic die cutting, or any other means.

Rear strap may further include an adjustment portion 161 with indicators 163 and connecting portion 166. Adjustment portion 161 may connect with rear strap 160 at junction 164. Junction 164 may be an ultrasonic weld, stitching, gluing or other connecting means. Adjustment portion 161 may also adjustably removably connect to rear strap 160 by engaging with slot 168. Connecting portion 166 can slide through slot 168 and reconnect to adjustment portion 161 or rear strap 160.

Indicators 163 may have a size or configuration marking to signify to the patient what setting they have their chin strap adjusted to. FIG. 13 demonstrates an example of this feature.

Adjustment portion may preferably be constructed from a fabric. FIG. 11A shows a fabric 180. Adjustment portion may be constructed from a lamination of foam and fabric. Alternatively, adjustment portion may be constructed of elastic.

3. Chin Strap with Cantilevered Jaw Support

In an example, a chin strap may provide a cantilevered jaw support via a semi-rigid cantilevered structure. The cantilevered jaw support may provide rigidity in the direction of the cantilever, but allow deformation or flexibility in the lateral direction. Such support may be enhanced using anthropometric data, materials selection, ergonomic analysis, and/or styling.

Figure 17:
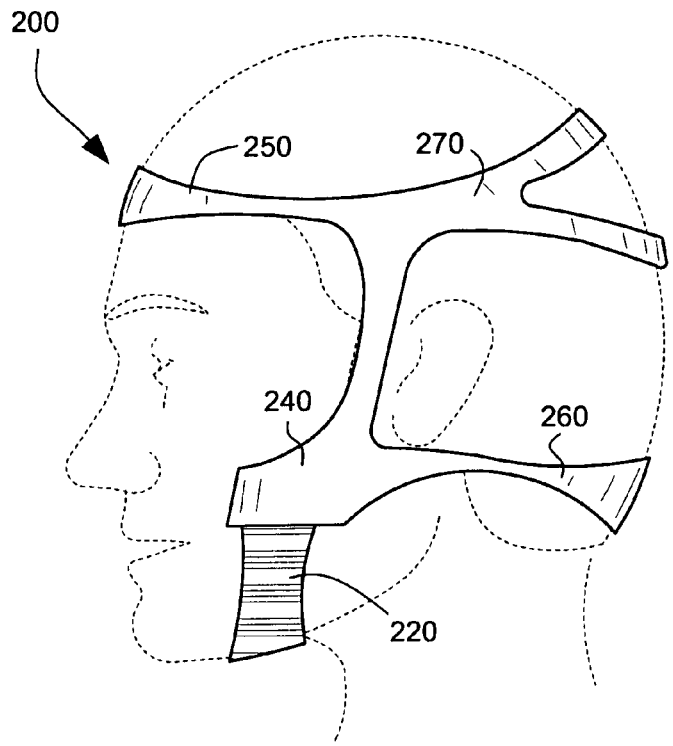
FIG. 17 is a side view of a chin strap arrangement in use according to another example of the present technology.

For example, FIG. 17 shows a chin strap arrangement 200 according to an example of the present technology. As illustrated, the chin strap arrangement 200 includes a side strap portion 240 adapted to extend along the patient's cheek and upwards forward of the patient's ear. Side strap portion 240 may be adapted to position chin strap portion 220 substantially perpendicular to the patient's chin so that the chin strap portion exerts a substantially vertical force on the patient's chin. Chin strap arrangement 200 may also include a lower rear strap portion 260 adapted to extend below the patient's ear and behind the patient's head. Lower rear strap portion 260 may be adapted to provide a lower horizontal headgear vector to stabilize the chin strap arrangement 200 on the patient's head. Chin strap arrangement 200 may also include a forehead strap portion 250 adapted to extend along the patient's forehead, and adapted to provide an upper horizontal headgear vector to stabilize the chin strap arrangement 200 on the patient's head. Chin strap arrangement 200 may also include an upper rear strap portion 270 that may bifurcate into two straps adapted to extend behind the patient's head to stabilize the chin strap arrangement 200 on the patient's head by cupping the patient's crown. In an alternative example, upper rear strap portion 270 may be one strap, i.e., not bifurcate. Chin strap arrangement 200 may also include a chin strap portion 220 (e.g., elastic or fabric material) adapted to extend below the patient's chin. Chin strap portion 220 is positioned to exert a substantially vertical force on the patient's chin. Preferably, chin strap portion 220 is positioned under the patient's chin or jaw. Preferably, chin strap portion 220 is constructed of an extensible material, such that if the patient needs to open their mouth (e.g., in the case of nose blockage), they can open their mouth by causing the chin strap portion 220 to stretch.

Figure 18:
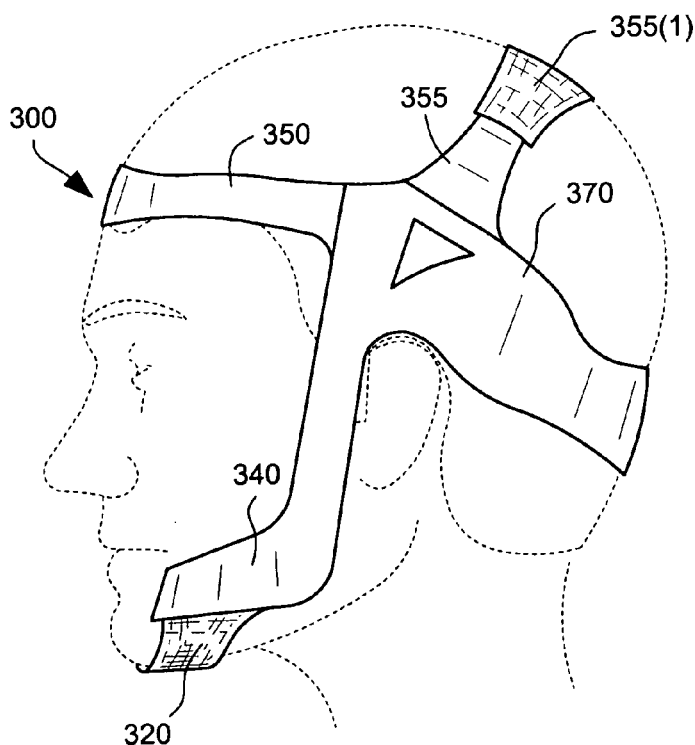
FIG. 18 is a side view of a chin strap arrangement in use according to another example of the present technology.

FIG. 18 shows a chin strap arrangement 300 according to another example of the present technology. As illustrated, the chin strap arrangement 300 includes a side strap portion 340 adapted to extend along the patient's cheek and upwards forward of the patient's ear, a forehead strap portion 350 adapted to extend along the patient's forehead, a rear strap portion 370 adapted to extend behind the patient's head, a top strap portion 355 adapted to extend over the top of the patient's head, and a chin strap portion 320 (e.g., elastic or fabric material) adapted to extend below the patient's chin. In an example, top strap portion 355 may include a cloth top 355(1), e.g., constructed of minimal elastic material. In an example, the side strap portion 340 and/or the rear strap portion 370 (e.g., formed in one-piece of a relatively rigid material) provide a conforming, relatively rigid structure or rigidizer that is structurally continuous along the side of the patient's face and/or around the rear of the patient's head and structured to allow a cantilevered jaw support at the patient's chin without rearward movement. In the illustrated example, each side strap portion 340 and cantilever aim form a general L-shape. In an example, the forehead strap portion 350 is constructed of an elastic material to maintain the rigid structure (i.e., rear strap portion) against the base of the patient's skull.

Figure 19:
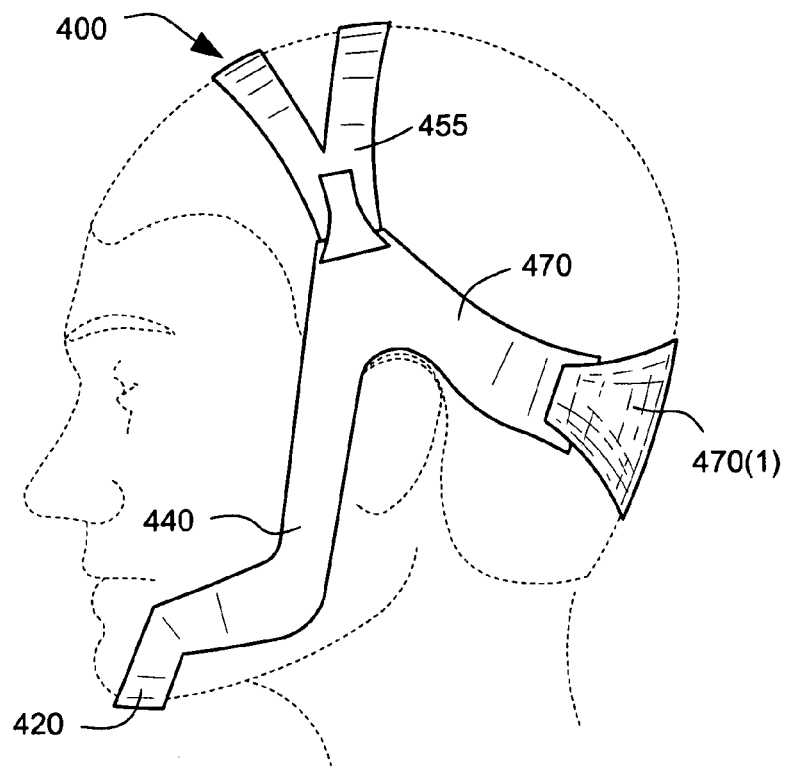
FIG. 19 is a side view of a chin strap arrangement in use according to another example of the present technology.

FIG. 19 shows a chin strap arrangement 400 according to another example of the present technology. As illustrated, the chin strap arrangement 400 includes a side strap portion 440 adapted to extend along the patient's cheek and upwards forward of the patient's ear, a rear strap portion 470 adapted to extend behind the patient's head, a top strap portion 455 that bifurcates into two straps adapted to extend over the top of the patient's head, and a chin strap portion 420 adapted to extend below the patient's chin. In an example, the side strap portion 440, the rear strap portion 470, and the chin strap portion 420 (e.g., formed in one-piece of a relatively rigid material) provide a conforming, relatively rigid structure or rigidizer that is structurally continuous around the rear of the patient's head and around the patient's mandible or lower jaw, and structured to allow a cantilevered jaw support at the patient's chin without rearward movement. In an example, a cloth or fabric back 470(1) is provided to the rear strap portion 470 (e.g., cloth or fabric back 470(1) detachably connected to the rear strap portion 470, e.g., by hook and loop material). In an example, the straps of the top strap portion 455 are constructed of an elastic material to maintain the rigid structure (i.e., rear strap portion and chin strap portion) against the patient's face.

Figure 20:
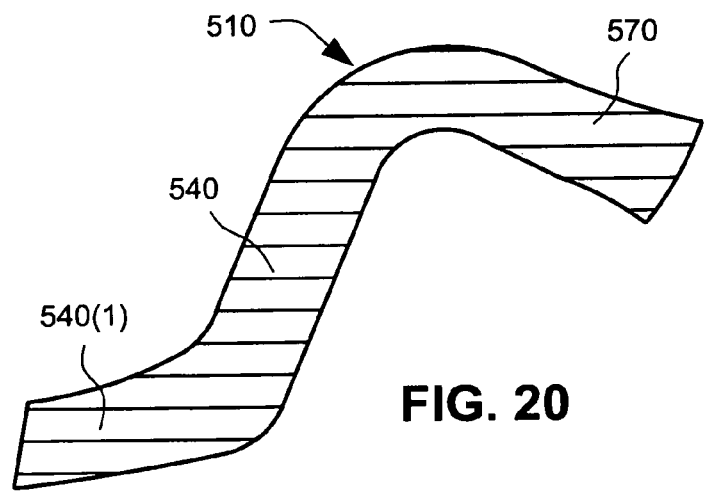
FIG. 20 is a side view of a relatively rigid structure for a chin strap arrangement according to an example of the present technology.
Figure 21:
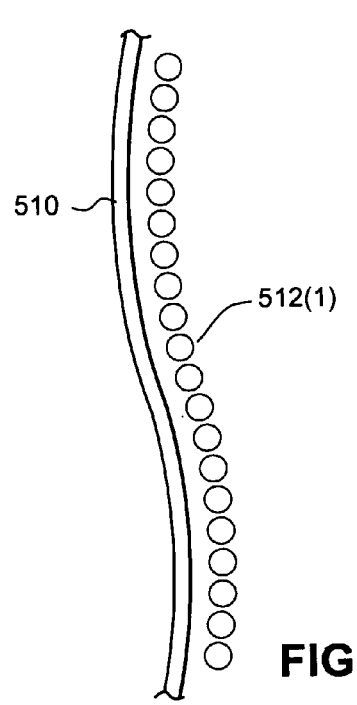
FIG. 21 shows a rigidizing element for the rigid structure of FIG. 20 according to an example of the present technology.
Figure 22:
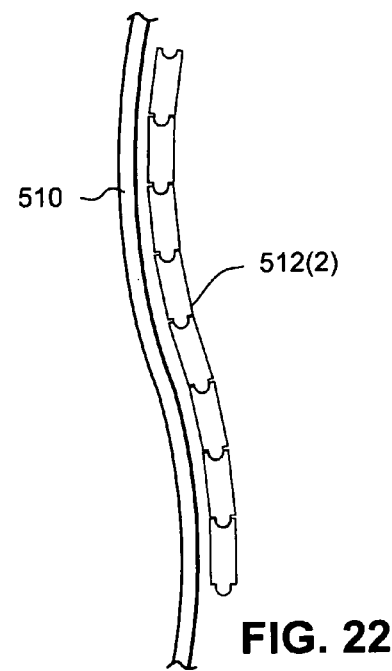
FIG. 22 shows a rigidizing element for the rigid structure of FIG. 20 according to another example of the present technology.

FIG. 20 illustrates a relatively rigid structure or rigidizer 510 (e.g., constructed of plastic) for a chin strap arrangement according to an example of the present technology. As illustrated, the relatively rigid structure 510 is similar to that shown in FIG. 18 and includes a side strap portion 540 and a rear strap portion 570. The side strap portion 540 provides a cantilever arm or cantilevered rigid portion 540(1) to cantilever the chin via a chin strap. In an example, one or more portions of the relatively rigid structure may be further rigidized or stabilized with a rigidizing element. Such rigidizing element may further rigidize or stabilize the rigid structure (e.g., to prevent twisting when cantilevered), while being sufficiently compliant to conform to the patient's face in use. For example, FIG. 21 shows a rigid structure 510 with a rigidizing element 512(1) including a Mylar sheet (e.g., similar to a sushi mat), and FIG. 22 shows a rigidizing element 512(2) including band-like segments or links (e.g., similar to a watchband link). In each example, segments need not be similar in size nor shape, e.g., to vary or adjust rigidity.

Figure 23:
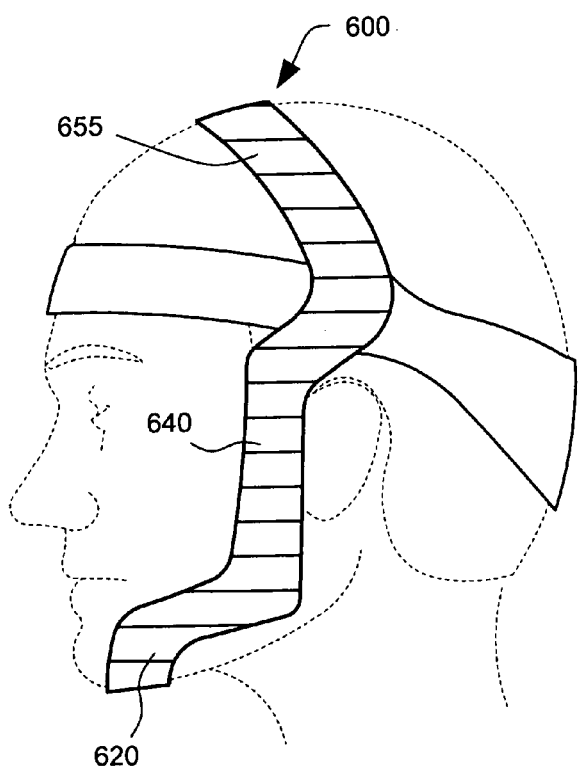
FIG. 23 is a side view of a chin strap arrangement in use according to another example of the present technology.

In an example, the chin strap arrangement may include a sling-type arrangement in which a top strap or top sling support adapted to extend over the top of the patient's head is arranged towards the front of the patient's skull rather than towards the rear of the patient's skull, e.g., to prevent rearward jaw displacement. For example, FIG. 23 shows a chin strap arrangement 600 with a top strap portion 655 oriented towards the front of the patient's skull. The chin strap arrangement provides a cantilevered chin strap portion 620 and a side strap portion 640 that extends outside the patient's face to keep the patient's face clear. In an alternative example, a simple sash/sling support may be provided along with headband to help retain stability and positioning.

In an example, a chin strap arrangement may be provided for use with a full-face mask system, e.g., chin strap arrangement provided or otherwise attached to existing mask headgear or chin strap arrangement integral with mask headgear. Such chin strap arrangement may support the full-face mask system and jaw together with minimal rearward force to minimize upper airway restriction.

In a further example, the chin strap arrangement may be adapted for use with a nasal mask and/or nasal pillows mask. In a further example, the chin strap arrangement may be adapted for use as a stand alone device for treating sleep disorders.

4. Chin Strap Example With Nasal Interface

Figure 24:
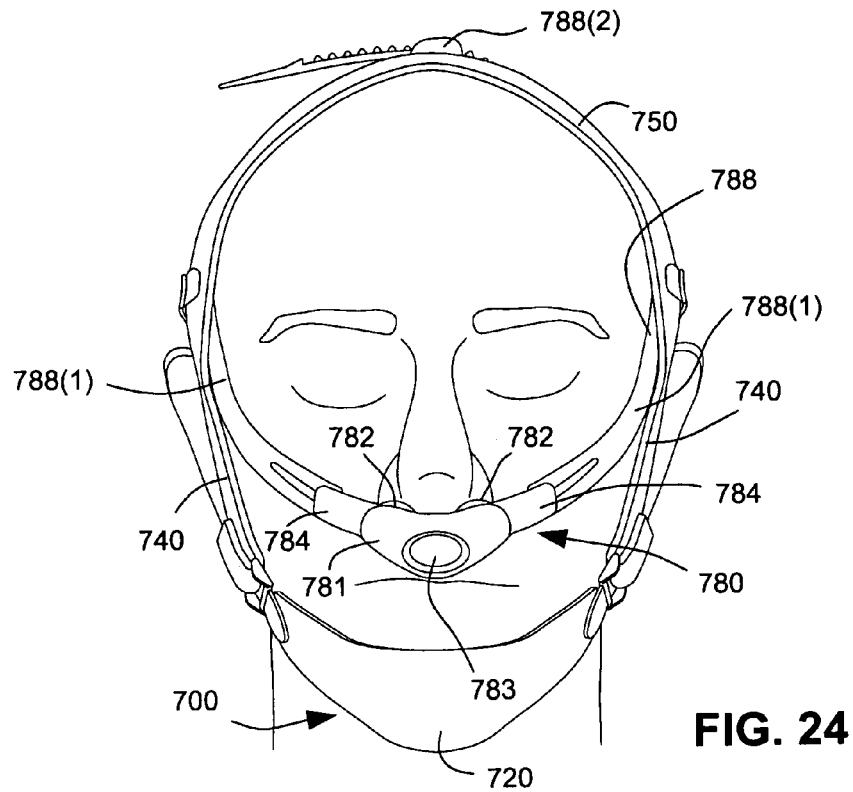
FIG. 24 is a front view of a mask system in use with a chin strap arrangement according to another example of the present technology.
Figure 25:
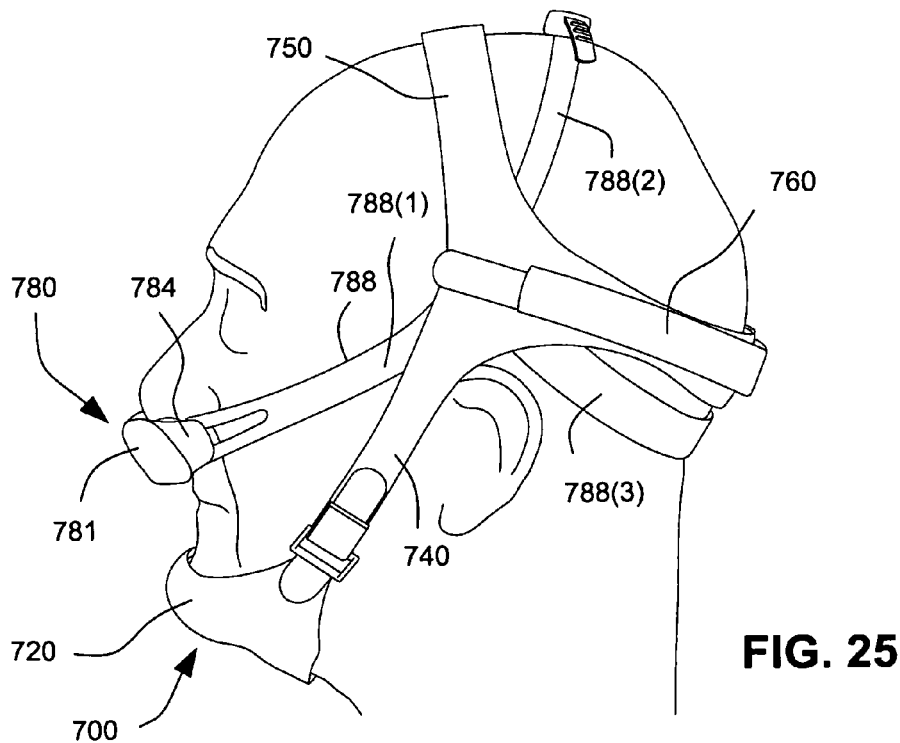
FIG. 25 is a side view of the mask system and chin strap arrangement of FIG. 24.
Figure 26:
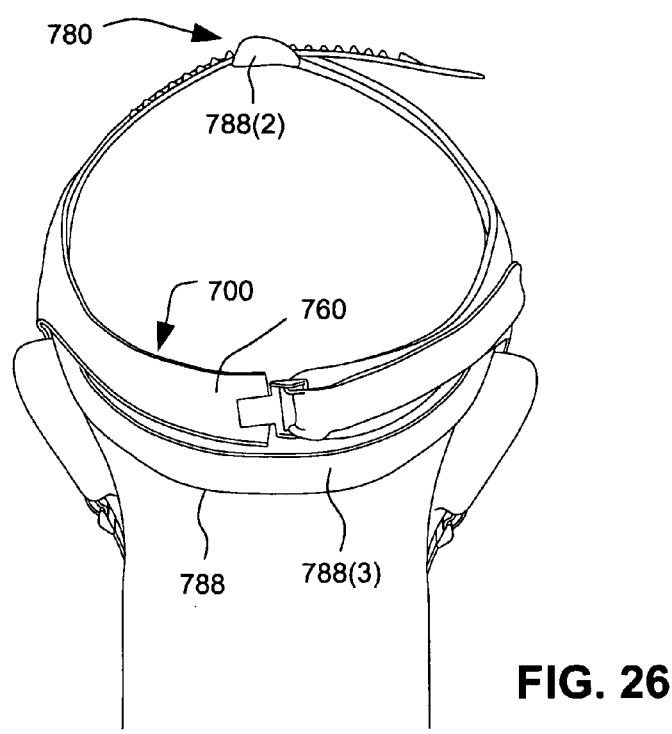
FIG. 26 is a rear view of the mask system and chin strap arrangement of FIG. 24.

FIGS. 24-26 show a chin strap arrangement 700 in use with a mask system 780 according to an example of the present technology. The mask system 780 includes a nozzle assembly 781 including nozzles or nasal pillows 782 adapted to form a seal with the patient's nares. The nozzle assembly includes an inlet or aperture 783 structured to communicate with an air delivery tube, e.g., via an elbow.

The nozzle assembly 781 also includes extensions 784 on each side that provide connectors for engaging headgear straps. Specifically, headgear 788 for the mask system includes side straps 788(1) coupled to respective connectors, a top strap 788(2), and a back strap 788(3). The free end of each side strap 788(1) includes a cut-out or aperture adapted to engage the connector.

Further details and examples of such mask system are disclosed in PCT Publication No. WO 2009/052560, which is incorporated herein by reference in its entirety.

The chin strap arrangement 700 includes a chin cup or chin engaging portion 720 and headgear including a pair of side straps 740, a top strap 750, and a rear strap 760. As illustrated, the sides straps 740 are adjustably coupled to the chin cup, e.g., via buckle arrangement, and the top and rear straps are adjustable, e.g., via a buckle arrangement and/or a locking arrangement. In an example, the chin cup is preformed to a shape that closely matches a patient's chin shape as described above.

In the illustrated example, the mask system 780 is first positioned on the patient's head and then the chin strap arrangement 700 is positioned over the mask system 780. However, it should be appreciated that the chin strap arrangement may be positioned underneath the mask system.

FIGS. 27-30 show the chin strap arrangement 700 in use with a mask system 880 according to another example of the present technology. The chin strap arrangement 700 is substantially similar to that described above and indicated with similar reference numerals. In this example, the mask system 880 is provided with a removable arm accessory which allows the mask system to attach to side straps of the chin strap arrangement, thereby allowing removal of headgear for the mask system to provide a simplified, less complicated system.

Figure 27:
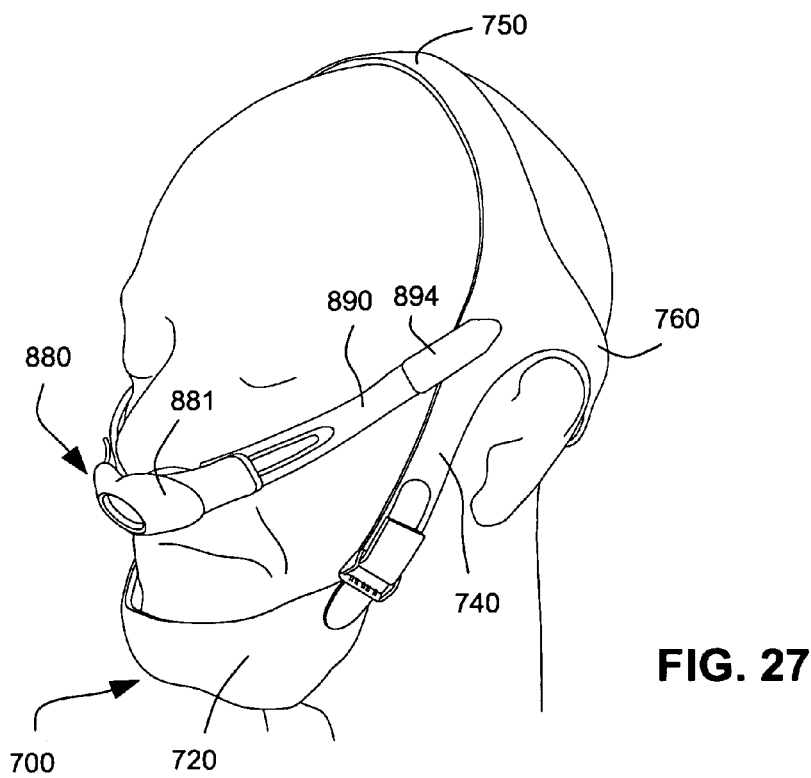
FIG. 27 is a perspective view of a mask system in use with a chin strap arrangement according to another example of the present technology.
Figure 28:
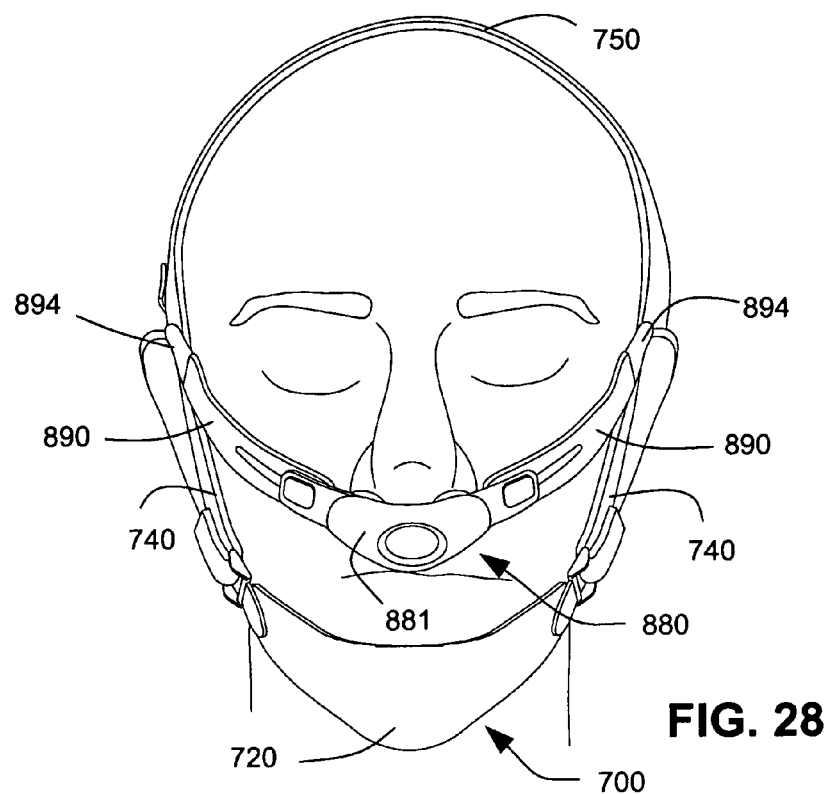
FIG. 28 is a front view of the mask system and chin strap arrangement of FIG. 27.
Figure 29:
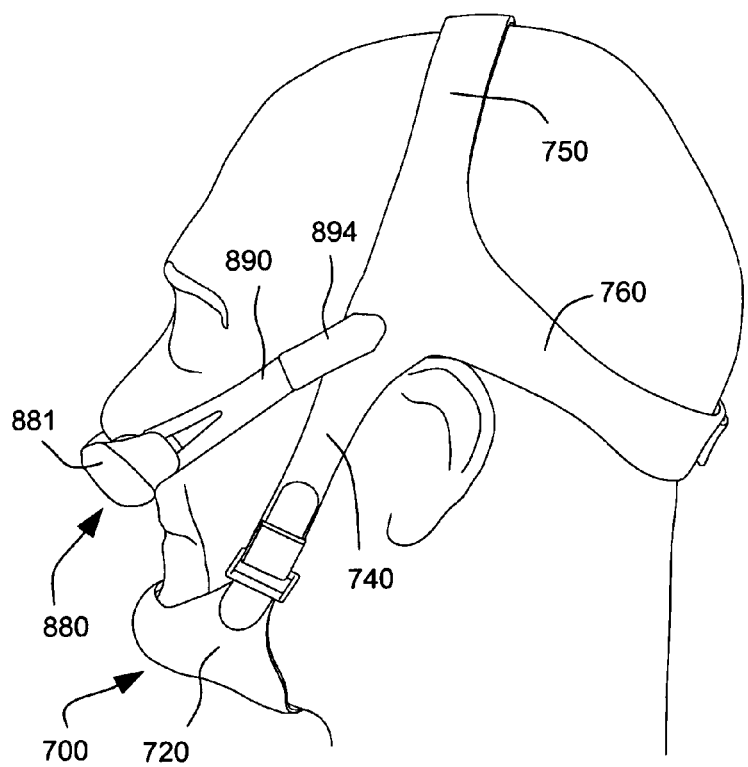
FIG. 29 is a side view of the mask system and chin strap arrangement of FIG. 27.
Figure 30:
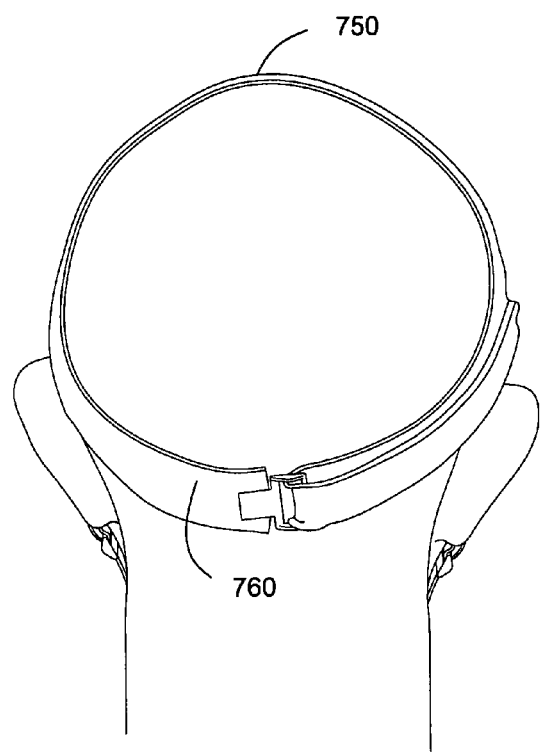
FIG. 30 is a rear view of the mask system and chin strap arrangement of FIG. 27.
Figure 31:
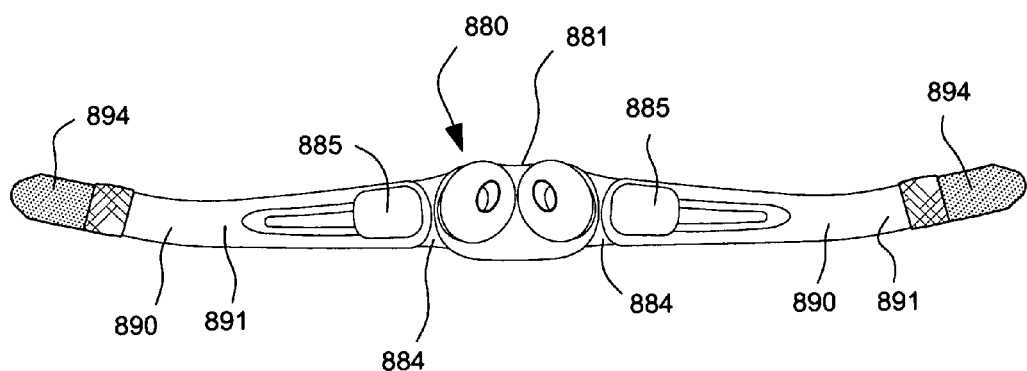
FIG. 31 is a top view of the mask system of FIG. 27.
Figure 32:
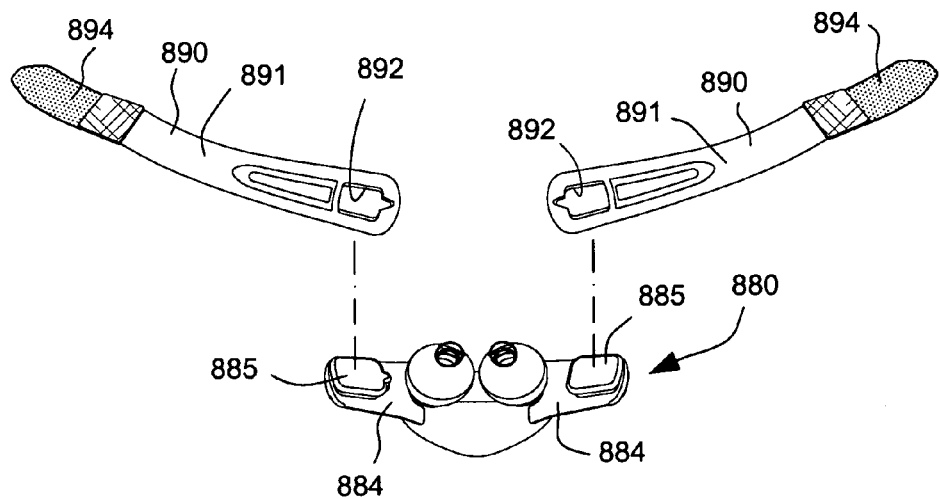
FIG. 32 is an exploded view of the mask system of FIG. 27.

As best shown in FIGS. 31 and 32, the mask system 880 includes the nozzle assembly 881 with extensions 884 on each side that provide connectors 885 as described above. In this example, a removable arm accessory including headgear strips or straps 890 are provided to the connectors 885, instead of the full headgear arrangement 788 described above. As illustrated, the strip 890 includes an elongated arm 891 (e.g., constructed of silicone) with one end having a cut-out or aperture 892 adapted to engage the connector 885, and the other end of the arm includes a tab of hook material 894. In use, as best shown in FIGS. 27-29, the mask system 880 may be attached to the chin strap arrangement 700 by attaching the hook material tabs 894 of the strips 890 to respective side straps 740 (e.g., constructed of loop material) of the chin strap arrangement 700.

The headgear strips 890 may be provided as an accessory, e.g., removable/interchangeable accessory for use with a chin strap arrangement.

Figure 33:
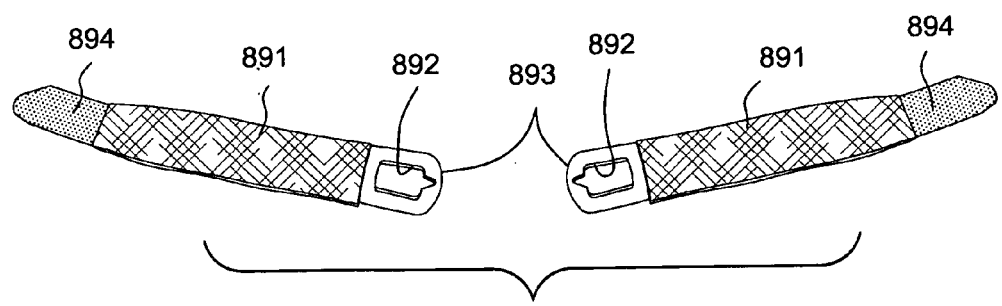
FIG. 33 is a top view of a removable arm accessory according to an example of the present technology.
Figure 34:
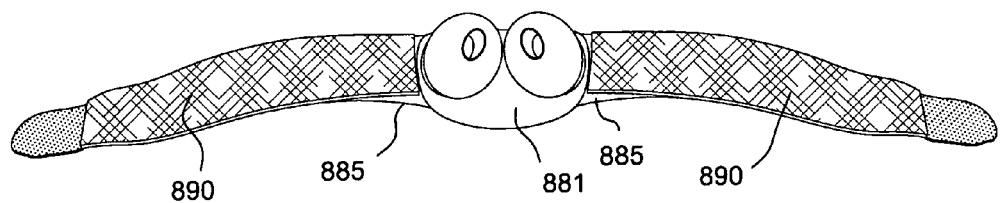
FIG. 34 is a top view of a mask system according to an example of the present technology.

In FIGS. 31 and 32, the arm 891 of the strip 890 is constructed of silicone with the hook material tab 894 molded onto the end thereof. In an alternative example, as shown in FIG. 33, the arm 891 of the strip may be constructed of a textile material, with silicone attachment portions 893 (providing cut-outs 892) molded onto the end thereof. In another alternative example, as shown in FIG. 34, ends of the strips 890 may be molded directly with the connectors 885 of the nozzle assembly 881.

Figure 35:
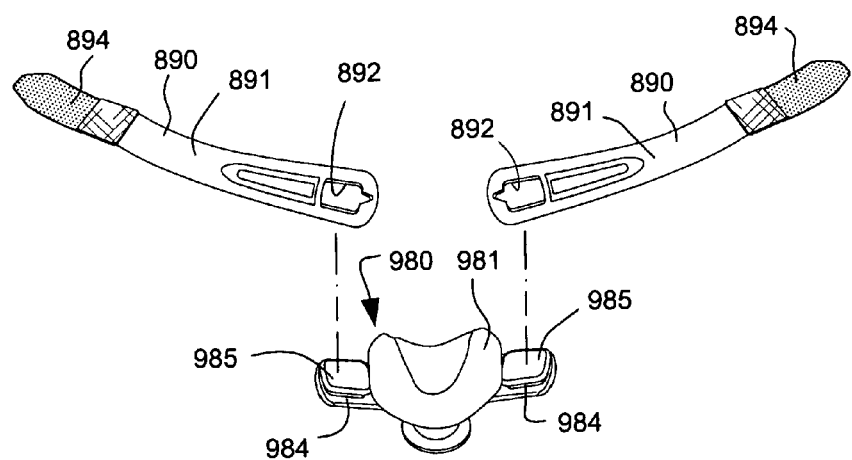
FIG. 35 is an exploded view of a mask system according to an example of the present technology.

The removable arm accessory may be usable with other interface types, i.e., interfaces may be exchangeable. For example, FIG. 35 shows the headgear strips 890 for use with a patient interface 980 including a sealing portion 981 that provides an under the nose sealing configuration. Similar to the nozzle assembly, the patient interface 980 includes extensions 984 on each side that provide connectors 985 for engaging the headgear strips 890. Further details and examples of such patient interface are disclosed in PCT Publication No. WO 2010/139014, which is incorporated herein by reference in its entirety. However, it should be appreciated that other interface types may be possible.

The removable arm accessory provides one or more of the following features: less cluttered system; increased user experience, usability, and intuitiveness; less visual bulk; and/or fewer parts. Also, the use of a hook and loop attachment for the removable arm accessory allows easy alignment of the sealing interface (e.g., nozzle assembly) to the patient's preferred vector, i.e., direct vector adjustment. In addition, the removable arm accessory provides relatively fast and easy application as the headgear strips can be applied and located without the sealing interface getting in the way, getting in the patient's eyes, and/or needing to be located at the start. Thus, the sealing interface can be quickly inserted and attached.

5. Alternative Examples

The patient's mouth or jaw may be shut or discouraged from opening by other means.

In an alternative example of the present technology, a pillow may be contoured or otherwise structured to provide jaw support that discourages opening, i.e., pillow which encourages mouth to stay closed. For example, the pillow may provide contouring, graded cushioning, and/or head/neck configuration to promote jaw closure, e.g., bolster or support on the pillow corner under the patient's jaw.

In another alternative example of the present technology, a lip adhesive or lip seal may be provided to the patient's lips to seal and maintain the patient's mouth closed during treatment. For example, the lip adhesive or lip seal may include one or more of the following: a lip gel to adhere or stick lips together; butterfly closure; mouth block; and/or gaffer tape. In an example, a chin strap may be used in conjunction with a device which stops the lips from breaching during breathing, e.g., lip seal.

In another alternative example, dental devices may be used to keep the mouth shut, e.g., mouth guards.

While the technology has been described in connection with several examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., one or more aspects of one example may be combined with aspects of another example to realize yet other examples. Further, each independent feature or component of any given assembly may constitute an additional example. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications

What is claimed is:

1. A chin strap arrangement for use in therapy for sleep disordered breathing, comprising:
    a side strap portion adapted to extend along the side of a patient's head and forward of a patient's ear and including a cantilever arm adapted to extend along a patient's cheek; and
    a chin strap portion provided to the cantilever arm and adapted to extend under a patient's chin,
    wherein the cantilever arm extends at an angle with respect to the side strap portion, and the chin strap portion extends from an anterior, bottom side of the cantilever arm,
    wherein the cantilever arm and the chin strap portion are configured to maintain a patient's mouth in a substantially closed position and support a patient's chin without rearward movement.

2. The chin strap arrangement according to claim 1, further comprising a rear strap portion adapted to extend above the patient's ear and behind the patient's head, and a top strap portion adapted to extend over the top of the patient's head.

3. The chin strap arrangement according to claim 2, wherein the side strap portion and the rear strap portion are formed in one piece of a relatively rigid material.

4. The chin strap arrangement according to claim 3, wherein the side strap portion and the rear strap portion provide a conforming, relatively rigid structure or rigidizer that is structurally continuous along the side of the patient's face and/or around the rear of the patient's head and structured to allow a cantilevered jaw support at the patient's chin without rearward movement.

5. The chin strap arrangement according to claim 3, further comprising a forehead strap portion adapted to extend along the patient's forehead, the forehead strap portion constructed of an elastic material to maintain the rear strap portion against the base of the patient's skull.

6. The chin strap arrangement according to claim 2, wherein the side strap portion, the rear strap portion, and the chin strap portion are formed in one piece of a relatively rigid material.

7. The chin strap arrangement according to claim 2, wherein the top strap portion includes a cloth top.

8. A patient interface for sealed delivery of a flow of breathable gas at a continuously positive pressure with respect to ambient air pressure to an entrance to the patient's airways including at least entrance of a patient's nares, wherein the patient interface is configured to maintain a therapy pressure above ambient air pressure in use, throughout the patient's respiratory cycle, while the patient is sleeping, to ameliorate sleep disordered breathing; said patient interface comprising:
    a sealing portion adapted to form a seal with at least one of the patient's nose and mouth; and
    a chin strap arrangement according to claim 1.

9. The patient interface according to claim 8, wherein the sealing portion includes a nozzle assembly including nozzles adapted to form a seal with the patient's nares.

10. The chin strap arrangement according to claim 1, further comprising a forehead strap portion adapted to extend along the patient's forehead.

11. The chin strap arrangement according to claim 1, wherein the chin strap portion is formed of an elastic material.

12. The chin strap arrangement according to claim 1, wherein the chin strap portion is formed of a fabric material.

13. The chin strap arrangement according to claim 1, wherein the cantilever arm is integral with the side strap portion.

14. The chin strap arrangement according to claim 1, wherein the cantilever arm includes one end anchored to the side strap portion and a free end opposite to the one end that projects from the side strap portion and adapted to extend along the patient's cheek.

15. The chin strap arrangement according to claim 1, wherein the chin strap portion is formed separately from the side strap portion and constructed of a more flexible material than the side strap portion.

16. A chin strap arrangement for use in therapy for sleep disordered breathing, comprising:
a side strap portion adapted to extend along the side of a patient's head and forward of a patient's ear;
a cantilever arm including one end anchored to the side strap portion and an opposite free end that projects from the side strap portion and adapted to extend along a patient's cheek; and
a chin strap portion extending from an anterior, bottom side of the cantilever arm and adapted to extend under a patient's chin,
wherein the cantilever arm and the chin strap portion are configured to maintain a patient's mouth in a substantially closed position and support a patient's chin without rearward movement.

17. The chin strap arrangement according to claim 16, further comprising a rear strap portion adapted to extend above the patient's ear and behind the patient's head, and a top strap portion adapted to extend over the top of the patient's head.

18. The chin strap arrangement according to claim 17, wherein the side strap portion and the rear strap portion are formed in one piece of a relatively rigid material.

19. A patient interface for sealed delivery of a flow of breathable gas at a continuously positive pressure with respect to ambient air pressure to an entrance to the patient's airways including at least entrance of a patient's nares, wherein the patient interface is configured to maintain a therapy pressure above ambient air pressure in use, throughout the patient's respiratory cycle, while the patient is sleeping, to ameliorate sleep disordered breathing; said patient interface comprising:
a sealing portion adapted to form a seal with at least one of the patient's nose and mouth; and
a chin strap arrangement according to claim 16.

20. The patient interface according to claim 19, wherein the sealing portion includes a nozzle assembly including nozzles adapted to form a seal with the patient's nares.

21. The chin strap arrangement according to claim 16, wherein the cantilever arm is integral with the side strap portion.

22. The chin strap arrangement according to claim 16, wherein the cantilever arm extends at an angle with respect to the side strap portion.

23. The chin strap arrangement according to claim 16, further comprising a forehead strap portion adapted to extend along the patient's forehead.

24. A chin strap arrangement for use in therapy for sleep disordered breathing, comprising:
a side strap portion adapted to extend along the side of a patient's head and forward of a patient's ear and including a cantilever arm adapted to extend along a patient's cheek; and
a chin strap portion provided to the cantilever arm and adapted to extend under a patient's chin,
wherein the cantilever arm extends at an angle with respect to the side strap portion, and the chin strap portion is provided to an anterior free end of the cantilever arm, wherein the cantilever arm and the chin strap portion are configured to maintain a patient's mouth in a substantially closed position and support a patient's chin without rearward movement.

25. A patient interface for sealed delivery of a flow of breathable gas at a continuously positive pressure with respect to ambient air pressure to an entrance to the patient's airways including at least entrance of a patient's nares, wherein the patient interface is configured to maintain a therapy pressure above ambient air pressure in use, throughout the patient's respiratory cycle, while the patient is sleeping, to ameliorate sleep disordered breathing; said patient interface comprising:
a sealing portion adapted to form a seal with at least one of the patient's nose and mouth; and
a chin strap arrangement according to claim 24.

26. The patient interface according to claim 25, wherein the sealing portion includes a nozzle assembly including nozzles adapted to form a seal with the patient's nares.

27. The chin strap arrangement according to claim 24, wherein the cantilever arm is integral with the side strap portion.

28. The chin strap arrangement according to claim 24, wherein the cantilever arm includes one end anchored to the side strap portion and the anterior free end is opposite to the one end and projects from the side strap portion and adapted to extend along the patient's cheek.

29. The chin strap arrangement according to claim 24, wherein the chin strap portion is formed separately from the side strap portion and constructed of a more flexible material than the side strap portion.

30. The chin strap arrangement according to claim 24, wherein each side strap portion and cantilever arm form a general L-shape and are constructed of a substantially rigid material.

31. A chin strap arrangement for use in therapy for sleep disordered breathing, comprising:
a side strap portion including a conforming, relatively rigid structure or rigidizer adapted to be structurally continuous along the side of a patient's face and structured to provide a cantilevered jaw support at a patient's chin without rearward movement,
the side strap portion including a cantilever arm adapted to extend along a patient's cheek, and
a chin strap portion provided to the cantilever arm and adapted to extend under the patient's chin and maintain a patient's mouth in a substantially closed position,
wherein the chin strap portion extends from an anterior, bottom side of the cantilever arm.

32. A patient interface for sealed delivery of a flow of breathable gas at a continuously positive pressure with respect to ambient air pressure to an entrance to the patient's airways including at least entrance of a patient's nares, wherein the patient interface is configured to maintain a therapy pressure above ambient air pressure in use, throughout the patient's respiratory cycle, while the patient is sleeping, to ameliorate sleep disordered breathing; said patient interface comprising:
a sealing portion adapted to form a seal with at least one of the patient's nose and mouth; and
a chin strap arrangement according to claim 31.

33. The patient interface according to claim 32, wherein the sealing portion includes a nozzle assembly including nozzles adapted to form a seal with the patient's nares.

34. The chin strap arrangement according to claim 31, wherein the cantilever arm includes one end anchored to the side strap portion and an opposite free end that projects from the side strap portion and adapted to extend along the patient's cheek.

35. A chin strap arrangement for use in therapy for sleep disordered breathing, comprising:

a pair of side strap portions each adapted to extend along the side of a patient's head and forward of a patient's ear and each including a cantilever arm adapted to extend along a patient's cheek; and a chin strap portion extending between the cantilever arms of the side strap portions and adapted to extend under a patient's chin, wherein each cantilever arm extends at an angle with respect to the respective side strap portion, and the chin strap portion is provided to the cantilever arms such that the chin strap portion extends anterior to a plane in which the side strap portions extend, wherein the cantilever arms and the chin strap portion are configured to maintain a patient's mouth in a substantially closed position and support a patient's chin without rearward movement.

36. A patient interface for sealed delivery of a flow of breathable gas at a continuously positive pressure with respect to ambient air pressure to an entrance to the patient's airways including at least entrance of a patient's nares, wherein the patient interface is configured to maintain a therapy pressure above ambient air pressure in use, throughout the patient's respiratory cycle, while the patient is sleeping, to ameliorate sleep disordered breathing; said patient interface comprising:

a sealing portion adapted to form a seal with at least one of the patient's nose and mouth; and a chin strap arrangement according to claim 35.

37. The patient interface according to claim 36, wherein the sealing portion includes a nozzle assembly including nozzles adapted to form a seal with the patient's nares.

38. The chin strap arrangement according to claim 35, wherein each side strap portion and cantilever arm form a general L-shape and are constructed of a substantially rigid material.

* * * * *